(12) United States Patent
Cascalho et al.

(10) Patent No.: US 11,214,603 B2
(45) Date of Patent: Jan. 4, 2022

(54) C3D CELLULAR AND ACELLULAR VACCINES FOR THE PREVENTION AND TREATMENT OF CANCER

(71) Applicant: The Regents of the University of Michigan, Ann Arbor, MI (US)

(72) Inventors: Marilia Cascalho, Ann Arbor, MI (US); Jeffrey L. Platt, Ann Arbor, MI (US)

(73) Assignee: THE REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 531 days.

(21) Appl. No.: 16/096,106

(22) PCT Filed: Apr. 18, 2017

(86) PCT No.: PCT/US2017/028155
§ 371 (c)(1),
(2) Date: Oct. 24, 2018

(87) PCT Pub. No.: WO2017/189281
PCT Pub. Date: Nov. 2, 2017

(65) Prior Publication Data
US 2019/0144514 A1    May 16, 2019

Related U.S. Application Data

(60) Provisional application No. 62/328,131, filed on Apr. 27, 2016.

(51) Int. Cl.
| | |
|---|---|
| C07K 14/47 | (2006.01) |
| A61K 38/17 | (2006.01) |
| A61K 35/13 | (2015.01) |
| A61K 39/395 | (2006.01) |
| C07K 16/28 | (2006.01) |
| A61P 35/00 | (2006.01) |
| A61K 45/06 | (2006.01) |
| A61K 39/00 | (2006.01) |

(52) U.S. Cl.
CPC ............ *C07K 14/472* (2013.01); *A61K 35/13* (2013.01); *A61K 38/1725* (2013.01); *A61K 39/3955* (2013.01); *A61K 45/06* (2013.01); *A61P 35/00* (2018.01); *C07K 16/2812* (2013.01); *C07K 16/2815* (2013.01); *C07K 16/2896* (2013.01); *A61K 2039/505* (2013.01); *A61K 2039/507* (2013.01); *A61K 2039/5152* (2013.01); *A61K 2039/54* (2013.01); *A61K 2039/545* (2013.01); *C07K 2317/75* (2013.01)

(58) Field of Classification Search
None
See application file for complete search history.

(56) References Cited

U.S. PATENT DOCUMENTS

| | | |
|---|---|---|
| 2004/0229827 A1 | 11/2004 | Steward et al. |
| 2008/0166379 A1 | 7/2008 | Lawman et al. |
| 2012/0064033 A1 | 3/2012 | Carroll et al. |
| 2014/0371302 A1 | 12/2014 | Afeyan et al. |

FOREIGN PATENT DOCUMENTS

| | | |
|---|---|---|
| WO | WO 1999/040925 | 8/1999 |
| WO | WO 2000/72686 | 12/2000 |
| WO | WO 2011/000551 | 1/2011 |

OTHER PUBLICATIONS

Xu et al. (Vaccine 28 (2010) 7221-7227). (Year: 2010).*
Balin et al. (Journal of Immunology, (Apr. 1, 2011) vol. 186, No. 1, Supp. MeetingAbstracts. Abstract No. 61.15). (Year: 2011).*
Bettelli, et al., Reciprocal developmental pathways for the generation of pathogenic effector TH17 and regulatory T cells. Nature. May 11, 2006;441 (7090):235-8.
Curiel, Tregs and rethinking cancer immunotherapy. J Clin Invest. May 2007;117(5): 1167-74.
Dempsey et al., C3d of complement as a molecular adjuvant: bridging innate and acquired immunity. Science. Jan. 19, 1996;271(5247):348-50.
Heeger et al., Decay-accelerating factor modulates induction of T cell immunity. J Exp Med. May 16, 2005;201 (10): 1523-30.
International Search Report and Written Opinion, International Patent Application No. PCT/US2017/028155, dated Jul. 19, 2017, 17 pages.
Janeway et al., Innate immune recognition. Annu Rev Immunol. 2002;20:197-216. Book: Table of Contents Provided.
Kaya et al., Contribution of the innate immune system to autoimmune myocarditis: a role for complement. Nat Immunol. Aug. 2001;2(8):739-45.
Kolev et al., Complement Regulates Nutrient Influx and Metabolic Reprogramming during Th1 Cell Responses. Immunity. Jun. 16, 2015;42(6):1033-47.
Kopf et al., Complement component C3 promotes T-cell priming and lung migration to control acute influenza virus infection. Nat Med. Apr. 2002;8(4):373-8.
Lambris et al. Mapping of the C3d receptor (CR2)-binding site and a neoantigenic site in the C3d domain of the third component of complement. Proc Natl Acad Sci U S A. Jun. 1985;82(12):4235-9.
Liu et al., The complement inhibitory protein DAF (CD55) suppresses T cell immunity in vivo. J Exp Med. Feb. 21, 2005;201(4):567-77.

(Continued)

*Primary Examiner* — Zachary S Skelding
(74) *Attorney, Agent, or Firm* — Casimir Jones, S.C.

(57) ABSTRACT

The present invention relates to the treatment of cancer and to the prevention of cancer growth and/or metastasis. In particular, the invention relates to cellular and acellular vaccines containing C3d, a proteolytic product of complement (C3), and methods of enhancing a host immune response (e.g., a T cell mediated immune response) against cancers using same. Compositions and methods of the invention find use, alone or in conjunction with other cancer therapies, in treating lymphoma and/or cancers that develop and/or persist by evading host immune surveillance and/or responses (e.g., T-cell mediated immune responses). Compositions and methods of the invention find use in both clinical and research settings, for example, within the fields of biology, immunology, medicine, and oncology.

12 Claims, 26 Drawing Sheets

(56) References Cited

OTHER PUBLICATIONS

Lyamani et al., A 16 amino-acid synthetic peptide, derived from human C3d, carries regulatory activity on in vitro phosphorylation of a cellular component of the human B lymphoma cells, Raji. Biochem Biophys Res Commun. Mar. 29, 1991;175(3):823-30.
Martin, Remington's Pharmaceutical Sciences, 15th Ed., Mack Publ. Co., Easton, Pa. (1975). Book: Table of Contents Provided.
Naidoo et al., Toxicities of the anti-PD-1 and anti-PD-L1 immune checkpoint antibodies. Ann Oncol. Dec. 2015;26(12):2375-91.
Ozinsky et al., The repertoire for pattern recognition of pathogens by the innate immune system is defined by cooperation between toll-like receptors. Proc Natl Acad Sci USA. Dec. 5, 2000;97(25):13766-71.
POSTOW et al., Immune Checkpoint Blockade in Cancer Therapy. J Clin Oncol. Jun. 10, 2015; 33(17): 1974-1982.
Pratt et al., Local synthesis of complement component C3 regulates acute renal transplant rejection. Nat Med. Jun. 2002;8(6):582-7.
Remington's Pharmaceutical Sciences, 18th ed., Mack 30 Publishing Co., Easton, Pa. (1990). Book: Table of Contents Provided.
Sambrook, J. et al., Molecular Cloning: A Laboratory Manual, 2nd ed., Cold Spring Harbor Laboratory Press, New York (1989) pp. 16.9-16.15. Book: Table of Contents Provided.
Servis et al., C3 synthetic peptides support growth of human CR2-positive lymphoblastoid B cells. J Immunol. Apr. 1, 1989;142(7):2207-12.
Zahid et al., Cell-type specific penetrating peptides: therapeutic promises and challenges. Molecules. Jul. 20, 2015;20(7): 13055-70.

\* cited by examiner

Vaccination with C3d-positive or C3d-negative killed melanoma cells

Vaccination with C3d-positive or C3d-negative killed melanoma cells

C3d - positive vaccine
Day 21

Foxp3-positive

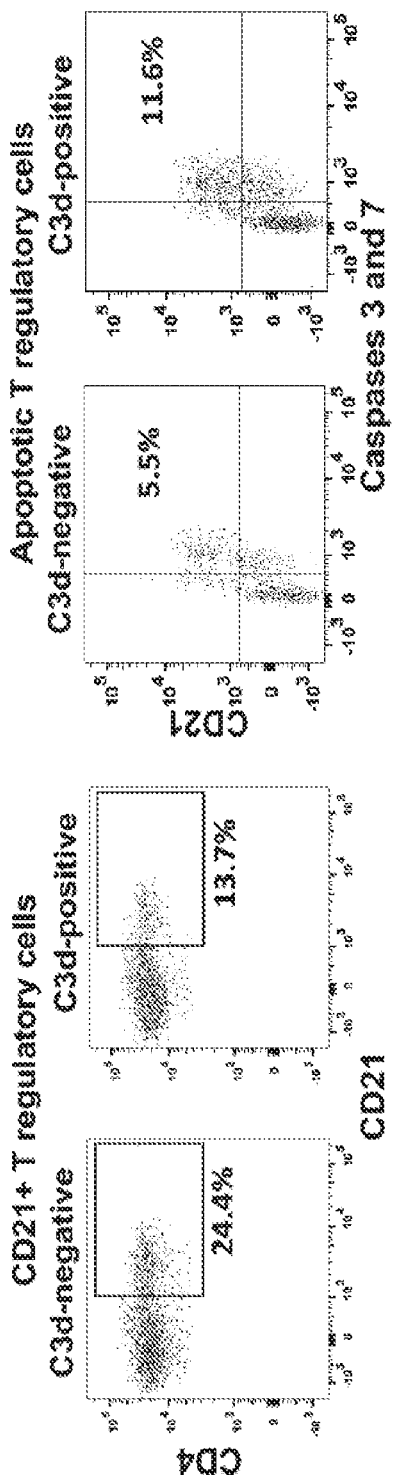
FIG. 3F
FIG. 3G
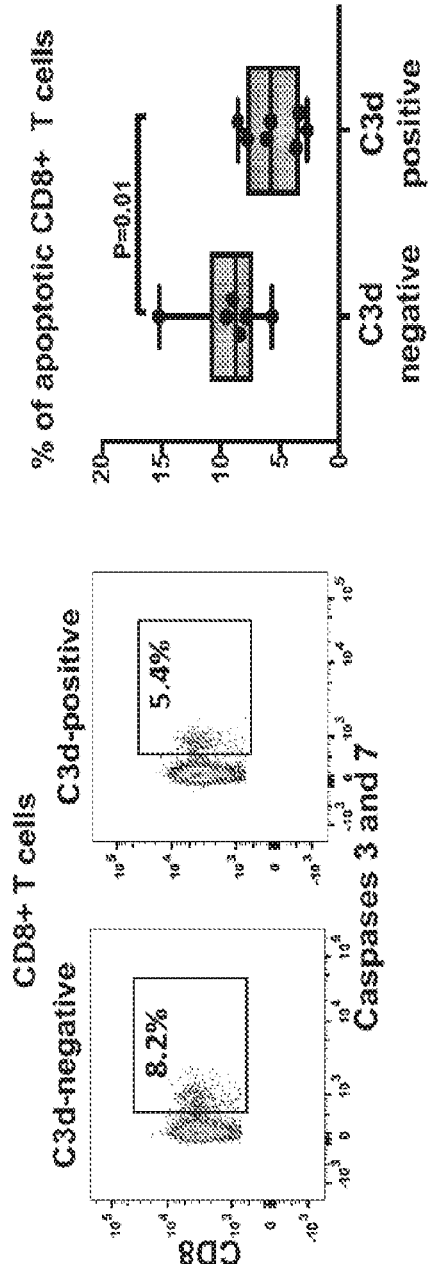
FIG. 3H
FIG. 3I

FIG. 6A
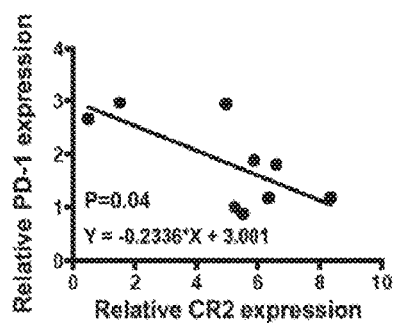
FIG. 6B
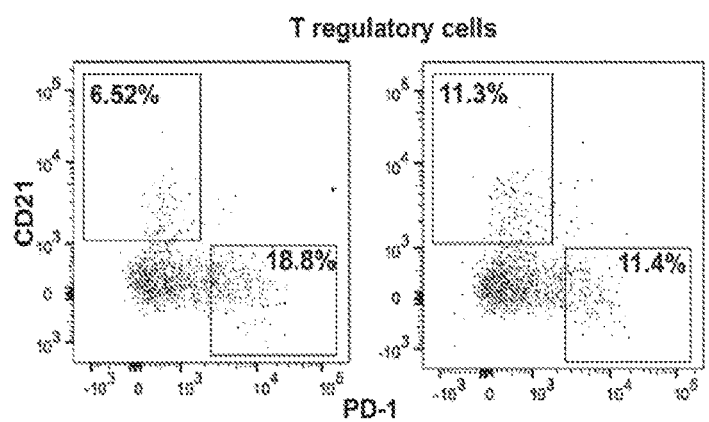
FIG. 6C
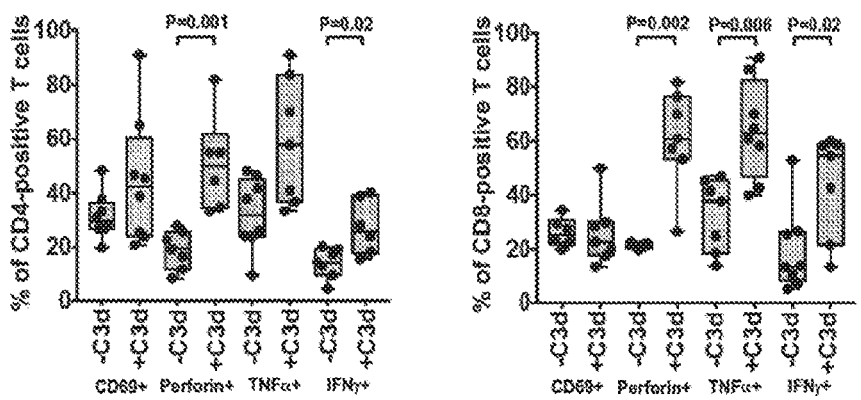
FIG. 6D
FIG. 6E
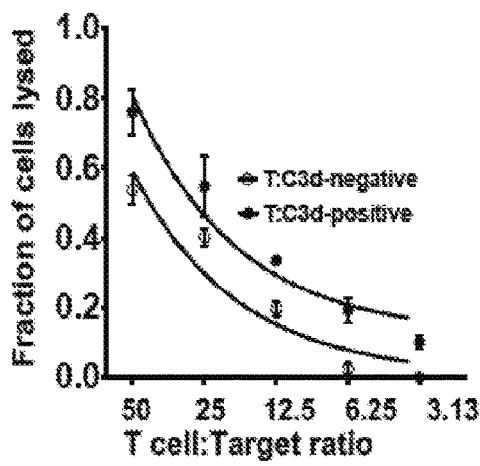

FIG. 8

```
          ----------+----------+----------+----------+
                   10         20         30         40
          ----------+----------+----------+----------+
  1   ACCCCCGCAGGCTCTGGGGAACAGAACATGATTGGCATGA   vectorC3d (SEQ ID NO:1)
  1   ............G...........................   C3dWT BL/6(SEQ ID NO:3)
  1   ............G.........C.................   BALB/c C3d(SEQ ID NO:5)

----------+----------+----------+----------+
                   50         60         70         80
          ----------+----------+----------+----------+
 41   CACCAACAGTCATTGCGGTACACTACCTGGACCAGACCGA   vectorC3d (SEQ ID NO:1)
 41   ........................................   C3dWT BL/6(SEQ ID NO:3)
 41   ........................................   BALB/c C3d(SEQ ID NO:5)

----------+----------+----------+----------+
                   90        100        110        120
          ----------+----------+----------+----------+
 81   ACAGTGGGAGAAGTTCGGCATAGAGAAGAGGCAAGAGGCC   vectorC3d (SEQ ID NO:1)
 81   ........................................   C3dWT BL/6(SEQ ID NO:3)
 81   ........G...............................   BALB/c C3d(SEQ ID NO:5)

----------+----------+----------+----------+
                  130        140        150        160
          ----------+----------+----------+----------+
121   CTGGAGCTCATCAAGAAAGGGTACACCCAGCAGCTGGCCT   vectorC3d (SEQ ID NO:1)
121   ........................................   C3dWT BL/6(SEQ ID NO:3)
121   ........................................   BALB/c C3d(SEQ ID NO:5)

----------+----------+----------+----------+
                  170        180        190        200
          ----------+----------+----------+----------+
161   TCAAACAGCCCAGCTCTGCCTATGCTGCCTTCAACAACCG   vectorC3d (SEQ ID NO:1)
161   ........................................   C3dWT BL/6(SEQ ID NO:3)
161   ........................................   BALB/c C3d(SEQ ID NO:5)

----------+----------+----------+----------+
                  210        220        230        240
          ----------+----------+----------+----------+
201   GCCCCCAGCACCTGGCTGACAGCCTACGTGGTCAAGGTC   vectorC3d (SEQ ID NO:1)
201   ........................................   C3dWT BL/6(SEQ ID NO:3)
201   ........................................   BALB/c C3d(SEQ ID NO:5)

----------+----------+----------+----------+
                  250        260        270        280
          ----------+----------+----------+----------+
241   TTCTCTCTAGCTGCCAACCTCATCGCCATCGACTCTCACG   vectorC3d (SEQ ID NO:1)
241   ........................................   C3dWT BL/6(SEQ ID NO:3)
241   ........................................   BALB/c C3d(SEQ ID NO:5)
```

FIG. 8 CONTINUED

```
         ----------+----------+----------+----------+
                 290        300        310        320
         ----------+----------+----------+----------+
281  TCCTGTGTGGGGCTGTTAAATGGTTGATTCTGGAGAAACA  vectorC3d (SEQ ID NO:1)
281  ........................................  C3dWT BL/6(SEQ ID NO:3)
281  ........................................  BALB/c C3d(SEQ ID NO:5)

----------+----------+----------+----------+
                 330        340        350        360
         ----------+----------+----------+----------+
321  GAAGCCGGATGGTGTCTTTCAGGAGGATGGGCCCGTGATT  vectorC3d (SEQ ID NO:1)
321  ........................................  C3dWT BL/6(SEQ ID NO:3)
321  ........................................  BALB/c C3d(SEQ ID NO:5)

----------+----------+----------+----------+
                 370        380        390        400
         ----------+----------+----------+----------+
361  CACCAAGAAATGATTGGTGGCTTCCGGAACGCCAAGGAGG  vectorC3d (SEQ ID NO:1)
361  ........................................  C3dWT BL/6(SEQ ID NO:3)
361  ........................................  BALB/c C3d(SEQ ID NO:5)

----------+----------+----------+----------+
                 410        420        430        440
         ----------+----------+----------+----------+
401  CAGATGTGTCACTCACAGCCTTCGTCCTCATCGCACTGCA  vectorC3d (SEQ ID NO:1)
401  ........................................  C3dWT BL/6(SEQ ID NO:3)
401  ........................................  BALB/c C3d(SEQ ID NO:5)

----------+----------+----------+----------+
                 450        460        470        480
         ----------+----------+----------+----------+
441  GGAAGCCAGGGACATCTGTGAGGGGCAGGTCAATAGCCTT  vectorC3d (SEQ ID NO:1)
441  ........................................  C3dWT BL/6(SEQ ID NO:3)
441  ........................................  BALB/c C3d(SEQ ID NO:5)

----------+----------+----------+----------+
                 490        500        510        520
         ----------+----------+----------+----------+
481  CCTGGGAGCATCAACAAGGCAGGGGAGTATATTGAAGCCA  vectorC3d (SEQ ID NO:1)
481  ........................................  C3dWT BL/6(SEQ ID NO:3)
481  ........................................  BALB/c C3d(SEQ ID NO:5)

----------+----------+----------+----------+
                 530        540        550        560
         ----------+----------+----------+----------+
521  GTTACATGAACCTGCAGAGACCATACACAGTGGCCATTGC  vectorC3d (SEQ ID NO:1)
521  ........................................  C3dWT BL/6(SEQ ID NO:3)
521  ........................................  BALB/c C3d(SEQ ID NO:5)
```

FIG. 8 CONTINUED

```
              ----------+----------+----------+----------+
                      570        580        590        600
              ----------+----------+----------+----------+
561  TGGGTATGCCCTGGCCCTGATGAACAAACTGGAGGAACCT  vectorC3d (SEQ ID NO:1)
561  ......................................  C3dWT BL/6(SEQ ID NO:3)
561  ......................................  BALB/c C3d(SEQ ID NO:5)

----------+----------+----------+----------+
                      610        620        630        640
              ----------+----------+----------+----------+
601  TACCTCGGCAAGTTTCTGAACACAGCCAAAGATCGGAACC  vectorC3d (SEQ ID NO:1)
601  ......................................  C3dWT BL/6(SEQ ID NO:3)
601  ......................................  BALB/c C3d(SEQ ID NO:5)

----------+----------+----------+----------+
                      650        660        670        680
              ----------+----------+----------+----------+
641  GCTGGGAGGAGCCTGACCAGCAGCTCTACAACGTAGAGGC  vectorC3d (SEQ ID NO:1)
641  ......................................  C3dWT BL/6(SEQ ID NO:3)
641  ......................................  BALB/c C3d(SEQ ID NO:5)

----------+----------+----------+----------+
                      690        700        710        720
              ----------+----------+----------+----------+
681  CACATCCTACGCCCTCCTGGCCCTGCTGCTGCTGAAAGAC  vectorC3d (SEQ ID NO:1)
681  ......................................  C3dWT BL/6(SEQ ID NO:3)
681  ......................................  BALB/c C3d(SEQ ID NO:5)

----------+----------+----------+----------+
                      730        740        750        760
              ----------+----------+----------+----------+
721  TTTGACTCTGTGCCCCCTGTAGTGCGCTGGCTCAATGAGC  vectorC3d (SEQ ID NO:1)
721  ......................................  C3dWT BL/6(SEQ ID NO:3)
721  ......................................  BALB/c C3d(SEQ ID NO:5)

----------+----------+----------+----------+
                      770        780        790        800
              ----------+----------+----------+----------+
761  AAAGATACTACGGAGGCGGCTATGGCTCCACCCAGGCTAC  vectorC3d (SEQ ID NO:1)
761  ......................................  C3dWT BL/6(SEQ ID NO:3)
761  ......................................  BALB/c C3d(SEQ ID NO:5)

----------+----------+----------+----------+
                      810        820        830        840
              ----------+----------+----------+----------+
801  CTTCATGGTATTCCAAGCCTTGGCCCAATATCAAACAGAT  vectorC3d (SEQ ID NO:1)
801  ......................................  C3dWT BL/6(SEQ ID NO:3)
801  ......................................  BALB/c C3d(SEQ ID NO:5)

----------+----------+----------+----------+
                      850        860        870        880
              ----------+----------+----------+----------+
841  GTCCCTGACCATAAGGACTTGAACATGGATGTGTCCTTCC  vectorC3d (SEQ ID NO:1)
841  ......................................  C3dWT BL/6(SEQ ID NO:3)
841  ......................................  BALB/c C3d(SEQ ID NO:5)
```

FIG. 8 CONTINUED

```
          ----------+--
                  890
          ----------+--
881 ACCTCCCCAGC  vectorC3d (SEQ ID NO:1)
881 ...........  C3dWT BL/6(SEQ ID NO:3)
881 ...........  BALB/c C3d(SEQ ID NO:5)
```

FIG. 9

```
         ----------+----------+----------+----------+
                  10         20         30         40
         ----------+----------+----------+----------+
  1 TPAGSGEQNMIGMTPTVIAVRYLDQTEQWEKFGIEKRQEA  vectorC3d  (SEQ ID NO:2)
  1 ....C...................................  C3dWT BL/6(SEQ ID NO:4)
  1 ....C...H...............G...............  BALB/c C3d(SEQ ID NO:6)

----------+----------+----------+----------+
                  50         60         70         80
         ----------+----------+----------+----------+
121 LELIKKGYTQQLAFKQPSSAYAAFNNRPPSTWLTAYVVKV  vectorC3d  (SEQ ID NO:2)
121 .......................................  C3dWT BL/6(SEQ ID NO:4)
121 .......................................  BALB/c C3d(SEQ ID NO:6)

----------+----------+----------+----------+
                  90        100        110        120
         ----------+----------+----------+----------+
241 FSLAANLIAIDSHVLCGAVKWLILEKQKPDGVFQEDGPVI  vectorC3d  (SEQ ID NO:2)
241 .......................................  C3dWT BL/6(SEQ ID NO:4)
241 .......................................  BALB/c C3d(SEQ ID NO:6)

----------+----------+----------+----------+
                 130        140        150        160
         ----------+----------+----------+----------+
361 HQEMIGGFRNAKEADVSLTAFVLIALQEARDICEGQVNSL  vectorC3d  (SEQ ID NO:2)
361 .......................................  C3dWT BL/6(SEQ ID NO:4)
361 .......................................  BALB/c C3d(SEQ ID NO:6)

----------+----------+----------+----------+
                 170        180        190        200
         ----------+----------+----------+----------+
481 PGSINKAGEYIEASYMNLQRPYTVAIAGYALALMNKLEEP  vectorC3d  (SEQ ID NO:2)
481 .......................................  C3dWT BL/6(SEQ ID NO:4)
481 .......................................  BALB/c C3d(SEQ ID NO:6)

----------+----------+----------+----------+
                 210        220        230        240
         ----------+----------+----------+----------+
601 YLGKFLNTAKDRNRWEEPDQQLYNVEATSYALLALLLLKD  vectorC3d  (SEQ ID NO:2)
601 .......................................  C3dWT BL/6(SEQ ID NO:4)
601 .......................................  BALB/c C3d(SEQ ID NO:6)

----------+----------+----------+----------+
                 250        260        270        280
         ----------+----------+----------+----------+
721 FDSVPPVVRWLNEQRYYGGGYGSTQATFMVFQALAQYQTD  vectorC3d  (SEQ ID NO:2)
721 .......................................  C3dWT BL/6(SEQ ID NO:4)
721 .......................................  BALB/c C3d(SEQ ID NO:6)

----------+----------
                 290
         ----------+----------
841 VPDHKDLNMDVSFHLPS  vectorC3d  (SEQ ID NO:2)
841 .................  C3dWT BL/6(SEQ ID NO:4)
841 .................  BALB/c C3d(SEQ ID NO:6)
```

C3D CELLULAR AND ACELLULAR VACCINES FOR THE PREVENTION AND TREATMENT OF CANCER

FIELD OF THE INVENTION

The present invention relates to the treatment of cancer and to the prevention of cancer growth and/or metastasis. In particular, the invention relates to cellular and acellular vaccines containing C3d, a proteolytic product of complement (C3), and methods of enhancing a host immune response (e.g., a T cell mediated immune response) against cancers using same. Compositions and methods of the invention find use in treating lymphoma and/or cancers that develop and/or persist by evading host immune surveillance and/or responses (e.g., T-cell mediated immune responses). Compositions and methods of the invention find use in both clinical and research settings, for example, within the fields of biology, immunology, medicine, and oncology.

BACKGROUND

Cancer is one of the most devastating diseases both in terms of human life opportunity loss and health care cost. It also presents unmet clinical needs. Cancer is typically treated with surgery, chemotherapy, radiation therapy, or a combination thereof. These treatments, however, often have significant side effects including immune system suppression, destruction of normal cells in the body, aberrant cellular metabolism, and even metastasis and the onset of secondary cancer.

Among the therapies currently used are some that manipulate the patient's own immune system potentially to attack the cancer. This overall approach is called cancer immunotherapy. Currently available cancer immunotherapies have limited efficacy and limited target patient population. Even the successful immunotherapies have shortcomings, some of which are similar to chemotherapies and some unique to cancer immunotherapy. Immunization is a principal feature for improving the health of people. Despite the availability of a variety of successful vaccines against many common diseases, cancer vaccines remain elusive.

SUMMARY OF THE INVENTION

The present invention relates to the treatment of cancer and to the prevention of cancer growth and/or metastasis. In particular, the invention relates to cellular and acellular vaccines containing C3d, a proteolytic product of complement (C3), and methods of enhancing a host immune response (e.g., a T cell mediated immune response) against cancer and/or lymphoma using same.

Accordingly, in one embodiment, the invention provides compositions (e.g., immunogenic compositions) for generating an immune response to cancer in a subject. In one embodiment, the composition is a cell based composition comprising cancer cells modified (e.g., genetically engineered) to express or to harbor C3d. In another embodiment, the composition is a cell based composition comprising cancer cells administered with isolated (e.g., recombinant) C3d. In still another embodiment, the composition is a cell based composition comprising cancer cells and further including one or more cell line(s) modified (e.g., genetically) to express C3d. In one embodiment, a cell based immunogenic composition comprises inactivated (e.g., irradiated) cancer cells (e.g., irradiated, whole cancer cells modified to express C3d). The invention is not limited by the means of inactivating cancer cells. Indeed, any means to inactivate cells known in the art may be used including those described herein.

In another embodiment, the invention provides an immunogenic composition comprising a tumor antigen (e.g., recombinant and/or isolated antigen) modified (e.g., genetically engineered) to be decorated with C3d (e.g., using chemical means). In another embodiment, the immunogenic composition comprises one or more cancer/tumor antigens and also includes isolated (e.g., recombinant) C3d. In still a further embodiment, the immunogenic composition comprises one or more cancer/tumor antigens and also includes a cell line(s) modified to express C3d.

In one embodiment, the invention provides an immunogenic composition comprising a cell lysate harvested from cancer cells expressing C3d. In another embodiment, the immunogenic composition comprises a cell lysate from cancer cell expressing C3d and also includes cancer cells (e.g., inactivated cancer cells). In another embodiment, the immunogenic composition comprises a cell lysate from cancer cell expressing C3d, further includes cancer cells, and also includes isolated (e.g., recombinant) C3d.

The invention is not limited by the type or form of C3d used. For example, in one embodiment, C3d expressed or harbored in a cell is free C3d (e.g., C3d polypeptide or oligomers of C3d polypeptide that are not part of a chimeric molecule encoding one or more specific antigens). C3d may be human C3d, non-human primate C3d, murine C3d, or other available C3d sequence. Full length C3d, or an immunostimulatory fragment thereof, may be used. For example, all or a portion of the nucleic acid sequence of SEQ ID NO. 1, SEQ ID NO. 3. and/or SEQ ID NO. 5 (e.g., shown in FIG. 8) may be used (e.g., to express (e.g., using an expression vector to express in vivo or in vitro) C3d). Any C3d peptide, or fragment thereof, that is immunostimulatory (e.g., that binds to CR2 and/or stimulates CR2 activity) finds use in the invention. For example, in some embodiments, C3d used in the compositions and methods of the invention comprises an amino acid sequence having at least 75%, 80%, 85%, 90%, 95%, 97%, 98%, 99% or more sequence identity to the amino acid sequence of SEQ ID NO: 2, SEQ ID NO: 4 or SEQ ID NO: 6 (e.g., shown in FIG. 9). In another embodiment, an immunostimulatory fragment of C3d used in the compositions and methods of the invention comprises an amino acid sequence having at least 75%, 80%, 85%, 90%, 95%, 97%, 98%, 99% or more sequence identity to the corresponding portion of the amino acid sequence of SEQ ID NO: 2, SEQ ID NO: 4 or SEQ ID NO: 6. The invention is not limited to any particular fragment of C3d. Indeed, any fragment of C3d that is known to be immunostimulatory (e.g., activate CR2) can be used including, but not limited to, those described herein. Furthermore, fragments of C3d can be assessed and identified as immunostimulatory (e.g., able to activate CR2) using methods well known to those in the art (e.g., methods described herein). In some embodiments, full length C3d, or an immunostimulatory fragment thereof, is used (e.g., is co-administered) with a one or more other CR2 agonists (e.g., to induce an immune response (e.g., to reduce immune tolerance and to induce an immune response (e.g., to stimulate and/or induce an anti-cancer immune response (e.g., a T cell mediated anti-cancer immune response)))) in the compositions and/or methods of the invention. The invention is not limited to any particular CR2 agonist. Indeed, any CR2 agonist known in the art may be used including, but not limited to, anti-CR2 agonist antibody (e.g., those described herein).

The invention also provides methods of manufacturing any one of the immunostimulatory/immunogenic compositions, or a combination thereof, described herein.

The invention further provides methods of using one or more of the immunogenic/immunostimulatory compositions of the invention for treating (e.g., therapeutically and/or prophylactically) cancer in a patient. In a further embodiment, following administration of an immunogenic composition of the invention to a patient, one or more immune responses to the cancer/tumor is detected (e.g., wherein the one or more immune responses are not detected the patient prior to administering the immunogenic composition). In yet a further embodiment, subsequent to detecting the one or more immune responses in the patient, treatment of the patient is modified (e.g., increased (e.g., the amount of cancer specific treatment (e.g., radiation, chemotherapy, surgical intervention) is augmented); decreased (e.g., the amount of cancer specific treatment (e.g., radiation, chemotherapy, surgical intervention) is reduced) and/or one or more additional treatments (e.g., the amount of cancer specific treatment (e.g., radiation, chemotherapy, surgical intervention) are started or discontinued.

The present invention is not limited by the type of cancer/tumor and/or lymphoma. Indeed, any cancer cell or tumor cell or lymphoma may be used, including, but not limited to, cells from cancer of the bladder, breast, colon, kidney, liver, lung, ovary, cervix, pancreas, rectum, prostate, stomach, epidermis; a hematopoietic tumor of lymphoid or myeloid lineage (e.g., leukemias, myelomas, and lymphomas); a tumor of mesenchymal origin such as a fibrosarcoma or rhabdomyosarcoma; other tumor types such as melanoma, teratocarcinoma, neuroblastoma, glioma, adenocarcinoma and/or non-small lung cell carcinoma.

Immunogenic/immunostimulatory compositions of the present invention can be used as vaccines to prevent diseases and as immunotherapeutics to treat diseases. In one embodiment, the invention provides a method of treating cancer in a subject (e.g., patient) comprising obtaining cancer/tumor cells from a subject harboring a cancer/tumor; modifying the cancer/tumor cells to render them capable of producing and/or harboring C3d or an immunostimulatory fragment thereof; inactivating the cancer/tumor cells (e.g., rendering the modified cancer/tumor cells proliferation incompetent); and administering the modified cancer/tumor cells to the subject from which the cancer/tumor cells were obtained. The invention is not limited by the order in which the above steps occur. For example, in one embodiment, cancer/tumor cells are obtained from a subject harboring a cancer/tumor; the cancer/tumor cells are inactivated (e.g., rendering the modified cancer/tumor cells proliferation incompetent); the inactivated tumor cells are then modified to harbor C3d (e.g., modifying the cancer/tumor cells to render them capable of producing and/or harboring C3d or an immunostimulatory fragment thereof); and then the modified cancer/tumor cells are administered to the subject from which the cancer/tumor cells were obtained. In another embodiment, the invention provides a method of treating cancer in a subject comprising obtaining cancer/tumor cells from a patient harboring cancer/tumor; modifying the cancer/tumor cells to render them capable of producing C3d; inactivating the cancer/tumor cells; and administering the modified cancer/tumor cells to a second, different subject from which the cancer/tumor cells were obtained. In one embodiment, cancer/tumor cells may be made to express C3d and optionally also a cancer therapeutic agent(s). In another embodiment, cancer/tumor cells made to express C3d are co-administered with a cancer therapeutic agent and/or are co-administered with separate cells made to express a cancer therapeutic agent. The invention is not limited by the means by which cells (e.g., autologous tumor cells) are modified to express or harbor C3d or other agent. For example, in one embodiment, a tumor cell is modified by introduction of a vector comprising a nucleic acid sequence encoding C3d, operably linked to a promoter and expression/control sequences necessary for expression thereof. In a further embodiment, the same autologous tumor cell is modified by introduction of a vector comprising a nucleic acid sequence encoding at least one tumor antigen or additional cancer therapeutic agent operably linked to a promoter and expression/control sequences necessary for expression thereof. In another embodiment, cells (e.g., cancer cells (e.g., allogenic cells or autologous cells) or cell lines) are modified to harbor C3d via conjugation of all or a portion of C3d to a protein transduction domain (PTD) and/or cell penetrating peptide (CPP) (e.g., so as to avoid introduction of foreign genetic material into the cells). The present invention is not limited by the type of PTD or CPP used. Indeed, any PTD or CPP known in the art can be used including, but not limited to, tissue-specific and non-tissue specific peptides including cationic peptides (e.g., of 6-12 amino acids in length comprised predominantly of arginine, ornithine and/or lysine residues); hydrophobic peptides (e.g., leader sequences of secreted growth factors or cytokines) and amphipathic peptides or cell-type specific peptides (e.g., obtained by linking hydrophobic peptides to nuclear localizing signals and/or identified via screening of peptide phage display libraries). PTDs and CPPs known in the art are described in Zahid and Robbins, Molecules 2015, 20(7), 13055-13070, hereby incorporated by reference in its entirety.

In yet another embodiment, the invention provides an immunogenic composition comprising gene-modified allogeneic cells (e.g., cells (e.g., a tumor cell line) derived from a subject other than the subject being treated) into which C3d encoding nucleic acid sequences have been introduced. In another embodiment, C3d sequences are introduced into separate (e.g., different) allogeneic tumor cell lines. The cell or population of cells may be from a tumor cell line of the same type as a tumor or cancer being treated in a subject.

In one embodiment, an immunogenic composition of the invention comprises a combination of autologous and allogenic cells (e.g., those described herein). Any ratio of allogenic to autologous cells may be used. In one embodiment, the ratio of allogeneic cells to autologous cancer cells in a given administration varies depending upon the combination.

The invention also provides compositions and methods for the treatment of cancer in a subject by administering an immunogenic composition (e.g., vaccine) of the invention and optionally one or more cancer therapeutic agents to a subject with cancer. The invention is not limited by the type of cancer therapeutic agent co-administered. Indeed, any cancer therapeutic known to those of skill in the art may be used including, but not limited to, those disclosed herein. In one embodiment, administration of an immunogenic composition (e.g., vaccine) and optionally one or more cancer therapeutic agents results in enhanced therapeutic efficacy and/or vaccine potency relative to administration of the immunogenic composition or the one or more cancer therapeutic agents alone. The invention is not limited by the route or frequency of administration of an immunogenic composition of the invention. Any suitable route of administration can be used to introduce an immunogenic composition of the invention into a subject including, but not limited to, intravenous, subcutaneous or intratumor administration, or other route or means described herein and/or known in the art. For example, local or systemic delivery can be accomplished by administration comprising administration of the combination into body cavities, by parenteral introduction, comprising intramuscular, intravenous, intraportal, intrahepatic, peritoneal, subcutaneous, and/or intradermal administration. An immunogenic composition of the invention may be administered proceeding, following, or in lieu of other treatments and/or therapies for treating and/or preventing cancer (e.g., preventing new cancer and/or the spread of cancer). In one embodiment, following administration, an immune response (e.g., cancer specific immune response) is detected wherein the immune response is not detected in a subject prior to administering the cellular composition. In another embodiment, subsequent to detecting one or more immune responses in a subject, treatment of the patient is modified based on the status of the immune response(s) detected in the patient.

The invention further provides compositions and kits comprising immunogenic compositions (e.g., vaccines) for use according to the description provided herein.

Vaccinated mice were challenged with C3d-negative tumor cells (expressing empty vector marker). (A) Frequency of apoptotic Treg (#CD4+, Foxp3+, caspase 3+ and 6+/#CD4+, Foxp3+ cells×100) in non-vaccinated or vaccinated mice determined by flow cytometry. (B) Tumor size (measured as areas) in the mice corresponding to the lymphocyte analysis. (C) Frequency of CD21+ Treg (#CD4+, CD21+, Foxp3+/#CD4+×100). (D) Plot compares the frequencies of CD21+ Treg with the respective tumor sizes. Each dot represents one mouse. (E) Frequency of T regs (#CD4+, Foxp3+/#CD4+×100) determined by flow cytometry. (F) Plot compares the frequencies of Treg with the respective tumor sizes. Each dot represents one mouse. Boxes in graphs represent distribution of data between the 25 and the 75 percentiles. The mean is indicated by a horizontal line and whiskers represent maximum and minimum values. Statistical analysis in A, B, C and E was by the Kruskal Wallis test followed by Dunns multiple comparison test.

Figure 5:
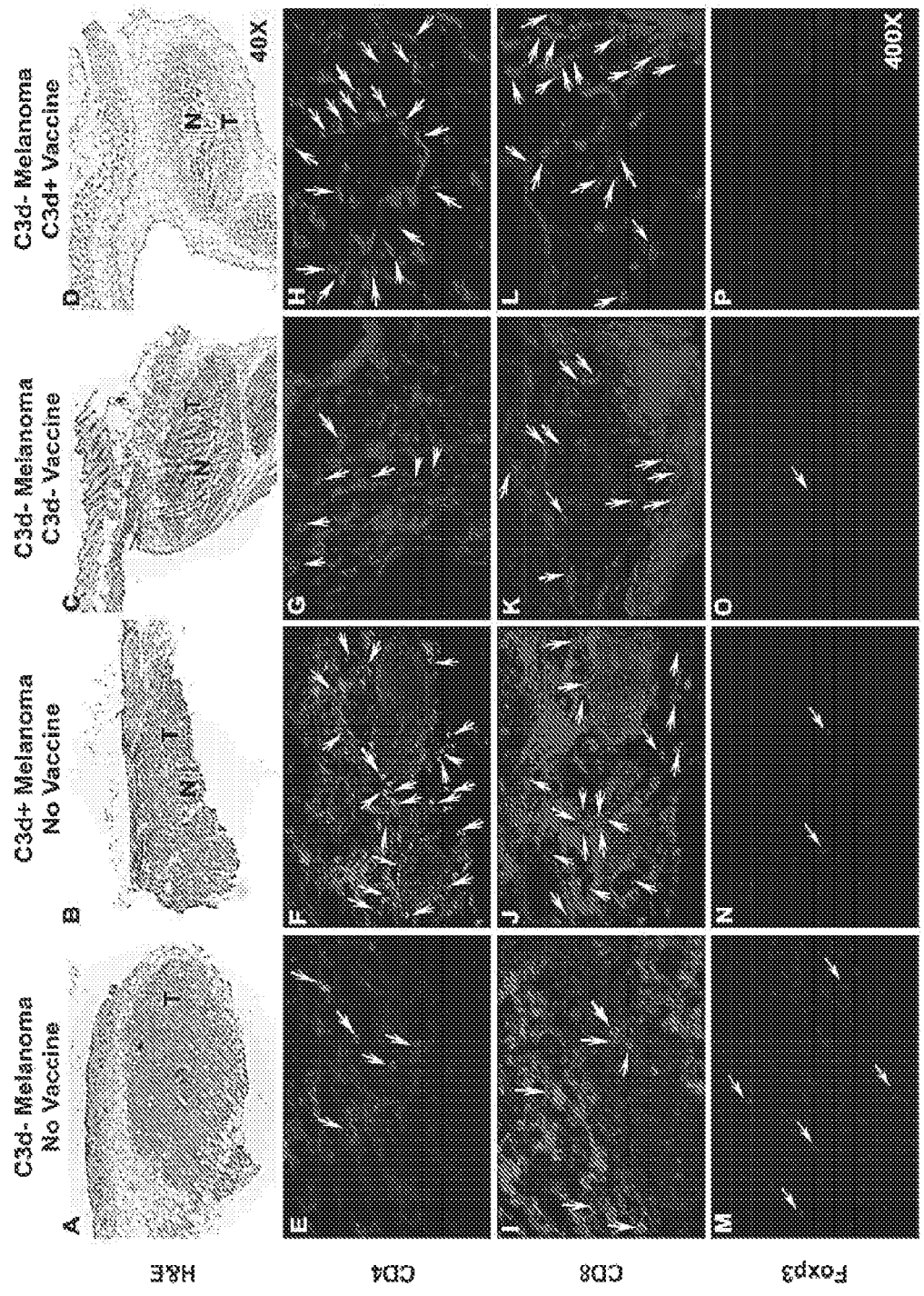

FIG. 5 shows that C3d expression by melanoma tumors enhances CD4+ and CD8+ lymphocytes but decreases the number of Treg in the tumor. Representative images of melanoma tumors expressing or not C3d (10 days after implantation), or of C3d− tumors (14 days after implantation) following C3d+ or C3d− vaccination 35 days prior to tumor implantation. A-D. Tumor nodules (T) in subcutaneous tissue. C3d+ and vaccine treated tumors have central necrosis (N) and an edematous stroma with brisk inflammation, (Hematoxilin and Eosin, 40×). E-H. Membrane staining for CD4 highlights $T_H$ cells in tumor and adjacent stroma. Examples of positive cells given by white arrows. (400×). I-L Membrane staining for CD8 highlights cytotoxic lymphocytes in tumor and adjacent stroma. Examples given by white arrows. Confluent staining is necrosis or keratin (400×). M-P Solid nuclear staining for Foxp3 highlights Treg cells in tumor and adjacent stroma. All positive cells highlighted by white arrows. Punctate staining is background (400×).

FIG. 6 shows that C3d modifies anti-tumor T cell functions. (A) CR2 and PD-1 expression measured by qPCR on regulatory T cells. Expression of CR2 and PD-1 were relative to that of GAPDH. (B) Flow cytometry analysis of lymphocytes obtained from the spleen of mice 10 days after injection of $5×10^3$ lymphoma cells. Figure shows reciprocal expression of CD21 and PD-1 by T regs (CD4+, Foxp3+). (C-D) Figure shows the percent (%) of CD4-positive (C) or CD8-positive (D) T cells isolated from the spleen of recipients of C3d+ or C3d− tumors that express perforin, TNFα and IFNγ, 3.5 hours after culture on anti-CD3 and anti-CD28 coated plates. Boxes in graphs represent distribution of data between the 25 and the 75 percentiles. The mean is indicated by a horizontal line and whiskers represent maximum and minimum values. Statistical analysis was by the Mann-Whitney 2 tailed test. (E) Cytotoxicity of splenic T cells isolated from lymphoma bearing mice were cultured with irradiated tumor cells, derived from the same clone that originated the tumors, in the presence of IL-2 for 6 days. Cytotoxicity against C3d+ or C3d− targets at various E:T ratios was measured by assaying release of LDH. Cytokine expression and cytotoxicity assays were repeated (3×) and performed at 3 different times, 3, 5 and 6 days. Controls to measure background lysis of responder or effector cells alone (by using an irrelevant target control) were subtracted from results.

Figure 7A:
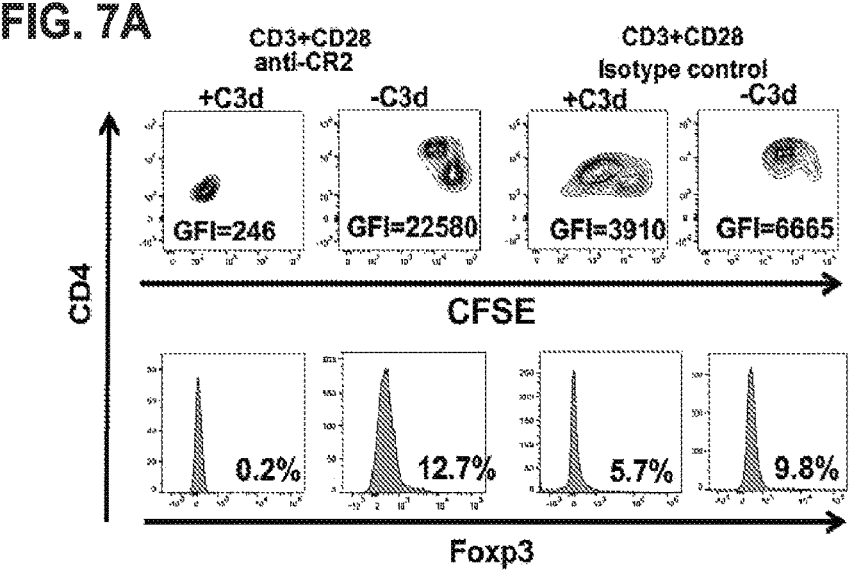
Figure 7B:
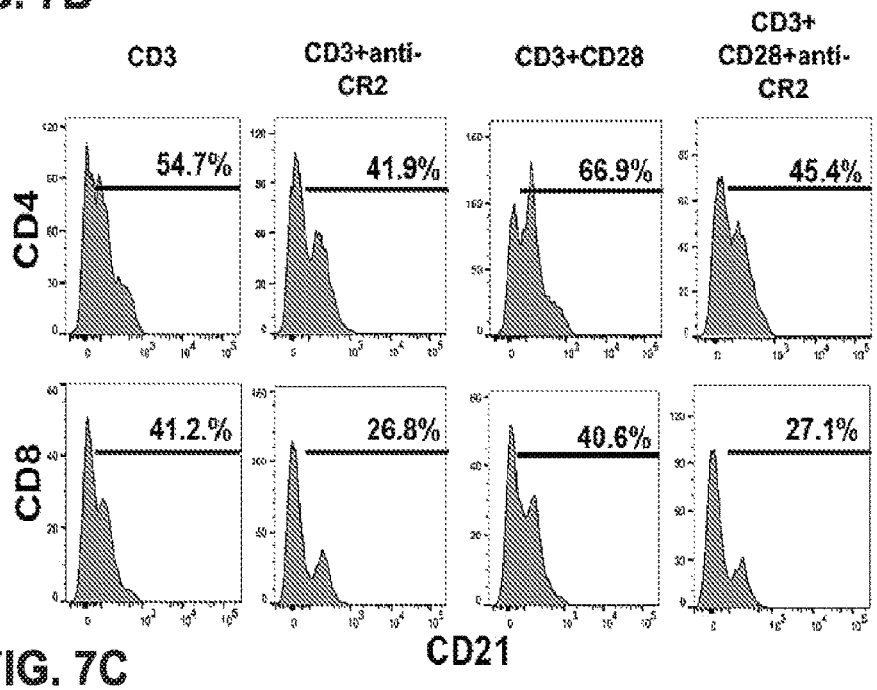

FIG. 7 shows the impact of C3d and agonist CR2 antibody on T cell functions and on survival of mice given lymphoma cells. Impact of free C3d on T cell proliferation stimulated with anti-CD3, anti-CD28 and IL2. T cells were magnetically isolated from spleens of naïve mice. (A) Figure shows flow cytometry analysis of CFSE or Foxp3 expression on gated CD4-positive cells after 5 days in culture, as indicated. The geometric fluorescence intensities (GFI) and the percentages of Foxp3+ cells are indicated. The figure is representative of 5 independent experiments. (B) Figure shows flow cytometry analysis of CD21 expression gated CD4+ or CD8+ T cells, following stimulation with anti CD3 and or anti CD28+/−anti CR2 for 5 days. Figure shows that anti CR2 decreases detection of expression of CD21 on the surface of lymphocytes. (C) Impact of anti-CR2 antibodies on survival of mice given C3d+ or C3d− lymphoma cells. Anti-CD21/CD35 (7G6) antibodies were administered at the same time as tumor cells. Figure represents Kaplan-Meier plots obtained for mice for each condition and differences between curves were analyzed by the Logrank Mantel-Cox test.

FIG. 8 shows the nucleic acid sequence of C3d (vectorC3d (SEQ ID NO: 1), See, e.g., Example 1) in one embodiment of the invention as well as murine C3d sequences (BL/6 (SEQ ID NO: 3) and BALB/c (SEQ ID NO: 5)).

FIG. 9 shows the amino acid sequence of C3d (vectorC3d (SEQ ID NO: 2), See, e.g., Example 1) in one embodiment of the invention as well as murine C3d sequences (BL/6 (SEQ ID NO: 4) and BALB/c (SEQ ID NO: 6)).

DEFINITIONS

To facilitate an understanding of the present invention, a number of terms and phrases are defined below:

As used herein the terms "disease" and "pathologic condition" are used interchangeably, unless indicated otherwise herein, to describe a deviation from the condition regarded as normal or average for members of a species or group (e.g., humans), and which is detrimental to an affected individual under conditions that are not inimical to the majority of individuals of that species or group. Such a deviation can manifest as a state, signs, and/or symptoms (e.g., diarrhea, nausea, fever, pain, blisters, boils, rash, immune suppression, inflammation, etc.) that are associated with any impairment of the normal state of a subject or of any of its organs or tissues that interrupts or modifies the performance of normal functions. A disease or pathological condition may be caused by or result from contact with a microorganism (e.g., a pathogen or other infective agent (e.g., a virus or bacteria)), may be responsive to environmental factors (e.g., malnutrition, industrial hazards, and/or climate), may be responsive to an inherent defect of the organism (e.g., genetic anomalies) or to combinations of these and other factors.

The terms "host," "subject," or "patient" as used herein, refer to an individual to be treated by (e.g., administered) the compositions and methods of the present invention. Subjects include, but are not limited to, mammals (e.g., murines, simians, equines, bovines, porcines, canines, felines, and the like), and most preferably includes humans. In the context of the invention, the term "subject" generally refers to an individual who will be administered or who has been administered one or more compositions of the present invention (e.g., a cellular or an acellular immunogenic composition comprising C3d or immunologically active fragment thereof).

The terms "buffer" or "buffering agents" refer to materials, that when added to a solution, cause the solution to resist changes in pH.

The terms "reducing agent" and "electron donor" refer to a material that donates electrons to a second material to reduce the oxidation state of one or more of the second material's atoms.

The term "monovalent salt" refers to any salt in which the metal (e.g., Na, K, or Li) has a net 1+ charge in solution (i.e., one more proton than electron).

The term "divalent salt" refers to any salt in which a metal (e.g., Mg, Ca, or Sr) has a net 2+ charge in solution.

The terms "chelator" or "chelating agent" refer to any materials having more than one atom with a lone pair of electrons that are available to bond to a metal ion.

The term "solution" refers to an aqueous or non-aqueous mixture.

As used herein, the term "a composition for inducing an immune response" refers to a composition that, once administered to a subject (e.g., once, twice, three times or more (e.g., separated by weeks, months or years)), stimulates, generates and/or elicits an immune response in the subject (e.g., resulting in total or partial immunity to and/or clearance of an immunogen (e.g., tumor) and/or prevents growth and/or metastasis of an immunogen (e.g., tumor) in a subject). A composition for inducing an immune response may comprise one or more other compounds or agents including, but not limited to, therapeutic agents, physiologically tolerable liquids, gels, carriers, diluents, adjuvants, excipients, salicylates, steroids, immunosuppressants, immunostimulants, antibodies, cytokines, antibiotics, binders, fillers, preservatives, stabilizing agents, emulsifiers, and/or buffers. An immune response may be an innate (e.g., a non-specific) immune response or a learned (e.g., acquired) immune response. Thus, in some preferred embodiments, a composition comprising a cellular or an acellular immunogenic composition comprising C3d is administered to a subject as a vaccine (e.g., to prevent or attenuate a disease (e.g., cancer (e.g., by eliminating or reducing tolerance by the host's immune system toward the cancer/tumor; or by providing to the subject total or partial immunity against the disease or the total or partial attenuation (e.g., suppression) of a sign, symptom or condition of the disease))).

As used herein, the terms "immunogen" and "antigen" may be used interchangeably to refer to an agent (e.g., whole cancer cells (e.g., modified to express C3d (e.g., that have been inactivated and/or killed (e.g., irradiated, undergone freeze-thaw lysis, and/or other type of cell membrane disruption)), homogenized cells, cell lysates, one or a plurality of protein components (e.g., isolated and/or purified and/or recombinant protein) of C3d or immunologically active fragment thereof, a tumor antigen (e.g., isolated and/or purified and/or recombinant tumor antigen), or microbial pathogens or pathogen products that cause cancer) that induces and/or stimulates an immune response either independently, or, in combination with other agents (e.g., an adjuvant, an immunostimulatory molecule (e.g., C3d), or other composition for stimulating an immune response). In preferred embodiments, immunogens elicit immunity against and/or clearance of, or prevent growth and/or metastasis of cancer (e.g., lymphoma) when administered as or in combination with an immunogenic composition of the present invention.

As used herein, the terms "cancer" and "tumor" refer to a cell that exhibits a loss of growth control (e.g., often forming large numbers of clones of the cell) or tissue of uncontrolled growth or proliferation of cells. Cancer and tumor cells generally are characterized by a loss of contact inhibition, may be invasive, and may display the ability to metastasize. The present invention is not limited by the type of cancer (e.g., prophylactically and/or therapeutically treated). Indeed, a variety of cancers may be treated with compositions and methods described herein including, but not limited to, melanomas, lymphomas, epithelial cancer, breast cancer, ovarian cancer, endometrial cancer, colorectal cancer, lung cancer, renal cancer, melanoma, kidney cancer, prostate cancer, brain cancer, sarcomas, carcinomas, and/or a combination thereof.

The term "inactivated," when used in reference to cells (e.g., cancer cells), refers to cells that have been rendered unable to proliferate or unable to undergo multiple rounds of mitosis, but that still retain the capability to express or display proteins (e.g., tumor antigens). Those of skill in the art know numerous methods for inactivating cells. In one non-limiting example, a cell based immunogenic composition of the invention, prior to administration to a subject, is irradiated (e.g., at a dose of from about 50 to about 200 rads/min or from about 120 to about 140 rads/min prior to administration to the subject). In one embodiment, the total level of irradiation utilized is around 2,500 rads, around 5,000 rads, around 10,000 rads, around 15,000 rads or around 20,000 rads, although lower and higher amounts may be used. Preferably, cells are irradiated with a total dose sufficient to inhibit substantially 100% of the cells from proliferating.

"Metastasis" as used herein refers to the process by which a cancer spreads or transfers from the site of origin to other regions of the body with the development of a similar cancerous lesion at the new location. A "metastatic" or "metastasizing" cell is one that loses adhesive contacts with neighboring cells and migrates via the bloodstream or lymph from the primary site of disease to invade neighboring body structures.

As used herein, the terms "tumor antigen" and "tumor immunogen" and "antigen from a cancer cell" and "tumor cell antigen" and grammatical equivalents may be used interchangeably to refer to any protein, carbohydrate or other component derived from or expressed by a tumor cell that is capable of eliciting an immune response.

As used herein, the term "adjuvant" refers to any substance that helps or that itself establishes a condition in which an immune response (e.g., anti-cancer immune response) to an antigen occurs. Some adjuvants can cause activation of a cell of the immune system (e.g., an adjuvant can cause a cell to produce and secrete a cytokine that helps the response of an immune cell to be initiated). Examples of adjuvants that can cause activation of a cell of the immune system include, but are not limited to, saponins purified from the bark of the Q. saponaria tree, such as QS21 (a glycolipid that elutes in the 21st peak with HPLC fractionation; Aquila Biopharmaceuticals, Inc., Worcester, Mass.); poly(di(carboxylatophenoxy)phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); and Leishmania elongation factor (a purified Leishmania protein; Corixa Corporation, Seattle, Wash.). Traditional adjuvants are well known in the art and include, for example, aluminum phosphate or hydroxide salts ("alum"). In some embodiments, vaccine compositions of the invention are administered with one or more adjuvants (e.g., to skew the immune response towards a Th1 and/or Th2 type response).

As used herein, the term "an amount effective to induce an immune response" (e.g., of a composition for inducing an immune response), refers to the dosage level required (e.g., when administered to a subject) to stimulate, generate and/or elicit an immune response in the subject. Thus, the term "therapeutically effective amount" or grammatical equivalents herein refers to an amount of the preparation that is sufficient to modulate the immune response of an individual or an amount sufficient to inhibit, suppress, hinder, retard or reverse progression of tumor growth. This amount may be different for different individuals, different tumor types, and different preparations. A "therapeutically effective amount" of a substance/molecule of the invention may vary according to factors such as the disease state, age, sex, and weight of the individual, and the ability of the substance/molecule, to elicit a desired response in the individual. A therapeutically effective amount encompasses an amount in which any toxic or detrimental effects of the substance/molecule are outweighed by the therapeutically beneficial effects. A "therapeutically effective amount" can be determined using procedures routinely employed by those of skill in the art such that an "improved therapeutic outcome" results. An effective amount can be administered in one or more administrations (e.g., via the same or different route), applications or dosages and is not intended to be limited to a particular formulation or administration route.

As used herein, the term "under conditions such that said subject generates an immune response" refers to any qualitative or quantitative induction, generation, and/or stimulation of an immune response (e.g., innate or acquired).

As used herein, the term "immune response" refers to a response by the immune system of a subject. For example, immune responses include, but are not limited to, a detectable alteration (e.g., increase or decrease) in T regulator cell (Treg) expression or total cell population/number, Toll-like receptor (TLR) activation, lymphokine (e.g., cytokine (e.g., Th1 or Th2 type cytokines) or chemokine) expression and/or secretion, macrophage activation, dendritic cell activation, T cell activation (e.g., CD4+ or CD8+ T cells), NK cell activation, and/or B cell activation (e.g., antibody generation and/or secretion). Additional examples of immune responses include binding of an immunogen (e.g., antigen (e.g., immunogenic polypeptide)) to an MHC molecule and inducing a cytotoxic T lymphocyte ("CTL") response, inducing a B cell response (e.g., antibody production), and/or T-helper lymphocyte response, and/or a delayed type hypersensitivity (DTH) response, (e.g., against an antigen from which an immunogen is derived), expansion (e.g., growth of a population of cells) or depletion (e.g., via programmed cell death) of cells of the immune system (e.g., T cells, B cells (e.g., of any stage of development (e.g., plasma cells), and increased processing and presentation of antigen by antigen presenting cells. An immune response may be directed against immunogens that the subject's immune system recognizes as foreign (e.g., non-self antigens (e.g., tumor antigens), or self-antigens (e.g., that a host fails to recognize (e.g., a tumor antigen)). Thus, it is to be understood that, as used herein, "immune response" refers to any type of immune response, including, but not limited to, innate immune responses (e.g., activation of Toll receptor signaling cascade), cell-mediated immune responses (e.g., responses mediated by T cells (e.g., antigen-specific T cells) and non-specific cells of the immune system), and humoral immune responses (e.g., responses mediated by B cells (e.g., via generation and secretion of antibodies into the plasma, lymph, and/or tissue fluids). The term "immune response" is meant to encompass all aspects of the capability of a subject's immune system to respond to immunogens (e.g., both the initial response to an immunogen (e.g., a tumor antigen) as well as acquired (e.g., memory) responses that are a result of an adaptive immune response).

As used herein, the terms "toll receptors" and "TLRs" refer to a class of receptors (e.g., TLR1, TLR2, TLR3, TLR4, TLR5, TLR6, TLR7, TLR8, TLR9, TLR10, TLR 11) that recognize special patterns of pathogens, termed pathogen-associated molecular patterns (See, e.g., Janeway and Medzhitov, (2002) Annu. Rev. Immunol. 20, 197-216). These receptors are expressed in innate immune cells (e.g., neutrophils, monocytes, macrophages, dendritic cells) and in other types of cells such as endothelial cells. Their ligands include bacterial products such as LPS, peptidoglycans, lipopeptides, and CpG DNA. TLRs are receptors that bind to exogenous ligands and mediate innate immune responses leading to the elimination of invading microbes. The TLR-triggered signaling pathway leads to activation of transcription factors including NFkB, which is important for the induced expression of proinflammatory cytokines and chemokines. TLRs also interact with each other. For example, TLR2 can form functional heterodimers with TLR1 or TLR6. The TLR2/1 dimer has a different ligand binding profile than the TLR2/6 dimer (Ozinsky et al., 2000). In some embodiments, an immunogenic composition of the invention activates cell signaling through a TLR (e.g., TLR2 and/or TLR4). Thus, in some embodiments, methods described herein include immunogenic compositions (e.g., cancer vaccines) that when administered to a subject, activates one or more TLRs and stimulates an immune response (e.g., innate and/or adaptive/acquired immune response) in a subject. Vaccine compositions described herein can in some embodiments activate TLRs (e.g., TLR2 and/or TLR4) by, for example, interacting with TLRs or activating any downstream cellular pathway that occurs upon binding of a ligand to a TLR. In some embodiments, vaccine compositions described herein that activate TLRs also enhance the availability or accessibility of any endogenous or naturally occurring ligand of TLRs. In some embodiments, vaccine compositions described herein that activate one or more TLRs alter transcription of genes, increase translation of mRNA or increase the activity of proteins that are involved in mediating TLR cellular processes.

As used herein, the term "immunity" refers to protection from disease (e.g., preventing or attenuating (e.g., suppression) of a sign, symptom or condition of the disease (e.g., tumor or cancer growth and/or metastasis)) upon exposure a vaccine composition described herein. Immunity can be innate (e.g., non-adaptive (e.g., non-acquired) immune responses that exist in the absence of a previous exposure to an immunogen) and/or acquired/adaptive (e.g., immune responses that are mediated by T and/or B cells following a previous exposure to immunogen (e.g., that exhibit increased specificity and reactivity to the immunogen)).

As used herein, the term "enhanced immunity" refers to an increase in the level of adaptive and/or acquired immunity in a subject to a given immunogen following administration of a composition (e.g., composition for inducing an immune response of the present invention) relative to the level of adaptive and/or acquired immunity in a subject that has not been administered the composition (e.g., composition for inducing an immune response of the present invention).

As used herein, the terms "purified" or "to purify" refer to the removal of contaminants or undesired compounds from a sample or composition. As used herein, the term "substantially purified" refers to the removal of from about 70 to 90%, up to 100%, of the contaminants or undesired compounds from a sample or composition.

As used herein, the terms "administration" and "administering" refer to the act of giving a composition of the present invention (e.g., a composition for inducing an immune response) to a subject. Exemplary routes of administration to the human body include, but are not limited to, through the eyes (ophthalmic), mouth (oral), skin (transdermal), nose (nasal), lungs (inhalant), oral mucosa (buccal), ear, rectal, by injection (e.g., intravenously, subcutaneously, intraperitoneally, intratumorally, etc.), topically, and the like.

As used herein, the terms "co-administration" and "co-administering" refer to the administration of at least two agent(s) (e.g., an immunogenic composition of the invention and one or more other agents—e.g., an adjuvant) or therapies to a subject. In some embodiments, the co-administration of two or more agents or therapies is concurrent. In other embodiments, a first agent/therapy is administered prior to a second agent/therapy. In some embodiments, co-administration can be via the same or different route of administration. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

The terms "pharmaceutically acceptable" or "pharmacologically acceptable," as used herein, refer to compositions that do not substantially produce adverse reactions (e.g., toxic, allergic or immunological reactions) when administered to a subject.

As used herein, the term "pharmaceutically acceptable carrier" refers to any of the standard pharmaceutical carriers including, but not limited to, phosphate buffered saline solution, water, and various types of wetting agents (e.g., sodium lauryl sulfate), any and all solvents, dispersion media, coatings, sodium lauryl sulfate, isotonic and absorption delaying agents, disintrigrants (e.g., potato starch or sodium starch glycolate), polyethylene glycol, and the like. The compositions also can include stabilizers and preservatives. Examples of carriers, stabilizers and adjuvants have been described and are known in the art (See e.g., Martin, Remington's Pharmaceutical Sciences, 15th Ed., Mack Publ. Co., Easton, Pa. (1975), incorporated herein by reference).

As used herein, the term "pharmaceutically acceptable salt" refers to any salt (e.g., obtained by reaction with an acid or a base) of a composition of the present invention that is physiologically tolerated in the target subject. "Salts" of the compositions of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzene-sulfonic acid, and the like. Other acids, such as oxalic, while not in themselves pharmaceutically acceptable, may be employed in the preparation of salts useful as intermediates in obtaining the compositions of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4+$, wherein W is C1-4 alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na+$, $NH_4+$, and $NW_4+$ (wherein W is a C1-4 alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

For therapeutic use, salts of the compositions of the present invention are contemplated as being pharmaceutically acceptable. However, salts of acids and bases that are non-pharmaceutically acceptable may also find use, for example, in the preparation or purification of a pharmaceutically acceptable composition.

As used herein, the term "at risk for disease" refers to a subject that is predisposed to experiencing a particular disease. This predisposition may be genetic (e.g., a particular genetic tendency to experience the disease, such as heritable disorders), or due to other factors (e.g., environmental conditions, exposures to detrimental compounds present in the environment, etc.). Thus, it is not intended that the present invention be limited to any particular risk (e.g., a subject may be "at risk for disease" simply by being exposed to and interacting with other people), nor is it intended that the present invention be limited to any particular disease (e.g., cancer).

As used herein, the term "kit" refers to any delivery system for delivering materials. In the context of immunogenic agents (e.g., an immunogenic composition of the invention), such delivery systems include systems that allow for the storage, transport, or delivery of immunogenic agents and/or supporting materials (e.g., written instructions for using the materials, etc.) from one location to another. For example, kits include one or more enclosures (e.g., boxes) containing the relevant immunogenic agents (e.g., cellular and/or acellular immunogenic compositions containing C3d) and/or supporting materials. As used herein, the term "fragmented kit" refers to delivery systems comprising two or more separate containers that each contain a subportion of the total kit components. The containers may be delivered to the intended recipient together or separately. For example, a first container may contain a composition comprising an immunogenic composition of the invention for a particular use, while a second container contains a second agent (e.g., an adjuvant). Indeed, any delivery system comprising two or more separate containers that each contains a subportion of the total kit components are included in the term "fragmented kit." In contrast, a "combined kit" refers to a delivery system containing all of the components of an immunogenic agent needed for a particular use in a single container (e.g., in a single box housing each of the desired components). The term "kit" includes both fragmented and combined kits.

As used herein, the term "immunoglobulin" or "antibody" refer to proteins that bind a specific antigen. Immunoglobulins include, but are not limited to, polyclonal, monoclonal, chimeric, and humanized antibodies, Fab fragments, F(ab')2 fragments, and includes immunoglobulins of the following classes: IgG, IgA, IgM, IgD, IgE, and secreted immunoglobulins (sIg). Immunoglobulins generally comprise two identical heavy chains and two light chains. However, the terms "antibody" and "immunoglobulin" also encompass single chain antibodies and two chain antibodies.

As used herein, the term "antigen binding protein" refers to proteins that bind to a specific antigen. "Antigen binding proteins" include, but are not limited to, immunoglobulins, including polyclonal, monoclonal, chimeric, and humanized antibodies; Fab fragments, F(ab')2 fragments, and Fab expression libraries; and single chain antibodies.

The term "epitope" as used herein refers to that portion of an antigen that makes contact with a particular immunoglobulin.

When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (e.g., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabeled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the terms "epithelial tissue" or "epithelium" refer to the cellular covering of internal and external surfaces of the body, including the lining of vessels and other small cavities. Epithelium is classified into types on the basis of the number of layers deep and the shape of the superficial cells.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received a preliminary diagnosis (e.g., a CT scan showing a mass or increased PSA level) but for whom a confirmatory test (e.g., biopsy and/or histology) has not been done or for whom the stage of cancer is not known. The term further includes people who once had cancer (e.g., an individual in remission). A "subject suspected of having cancer" is sometimes diagnosed with cancer and is sometimes found to not have cancer.

As used herein, the term "subject diagnosed with a cancer" refers to a subject who has been tested and found to possess cancerous cells. The cancer may be diagnosed using any suitable method, including but not limited to, biopsy, x-ray, blood test, etc.

As used herein, the term "post-surgical tumor tissue" refers to cancerous tissue (e.g., organ tissue) that has been removed from a subject (e.g., during surgery).

As used herein, the term "identifying the risk of said tumor metastasizing" refers to the relative risk (e.g., the percent chance or a relative score) of a tumor (e.g., prostate, colon, breast, etc. tumor) metastasizing.

As used herein, the term "subject at risk for cancer" refers to a subject with one or more risk factors for developing a specific cancer. Risk factors include, but are not limited to, gender, age, genetic predisposition, environmental exposure, and previous incidents of cancer, preexisting non-cancer diseases, and lifestyle.

As used herein, the term "characterizing cancer in subject" refers to the identification of one or more properties of a cancer sample in a subject, including but not limited to, the presence of benign, pre-cancerous or cancerous tissue and the stage of the cancer.

As used herein, the term "characterizing tissue in a subject" refers to the identification of one or more properties of a tissue sample (e.g., including but not limited to, the presence of cancerous tissue, the presence of pre-cancerous tissue that is likely to become cancerous, and the presence of cancerous tissue that is likely to metastasize).

As used herein, the term "stage of cancer" refers to a qualitative or quantitative assessment of the level of advancement of a cancer. Criteria used to determine the stage of a cancer include, but are not limited to, the size of the tumor, whether the tumor has spread to other parts of the body and where the cancer has spread (e.g., within the same organ or region of the body or to another organ).

As used herein, the term "primary tumor cell" refers to a cancer cell that is isolated from a tumor in a mammal and has not been extensively cultured in vitro.

As used herein, the term "target diseased cell" refers to (a) a cell causing, propagating, aggravating or contributing to a disease in a subject, (b) a cell capable of causing, propagating, aggravating or contributing to a disease in a subject, (c) a cell derived from (a) or (b), or (d) a cell sharing antigenic characteristics of (a) or (b). Target diseased cells may or may not be taken from the subject to be treated by a method of the invention. Target diseased cells include, but are not limited to, tumor cells (including unmodified tumor cells, tumor cells modified (e.g., genetically modified) with different approaches, primary cultures of tumor cells, and established cancer cell lines). The sources of tumor cells include, but are not limited to, lymphoma, melanoma, liver cancer, hepatocellular carcinoma, lung cancer, gastric cancer, colorectal carcinoma, renal carcinoma, head and neck cancers, sarcoma, leukemia, brain tumor and/or lymphoma, osteosarcoma, bladder carcinoma, myloma, breast cancer, prostate cancer, ovarian cancer, and pancreas carcinoma. In addition, target diseased cells include cells transformed or immortalized by irradiation, viral infection, exposure to carcinogens, and other means known to or to be developed by those skilled in the art.

As used herein, the term "autologous" refers to a target diseased cell from the subject, or from another subject having the same or highly similar major histocompatibility phenotype. An autologous target cell may be obtained from the subject or another source sharing the same WIC with methods known to those skilled in the art. Once taken from a patient, an autologous cell may be modified, transfected, and treated by methods described herein and other methods known to those skilled in the art.

As used herein, the terms "treatment", "therapeutic use", or "medicinal use" refer to any and all uses of the claimed compositions that remedy a disease state or symptoms, or otherwise prevent, hinder, retard, or reverse the progression of disease or other undesirable symptoms in any way whatsoever. For example, the terms "treatment of cancer" or "treatment of tumor" or grammatical equivalents herein are meant the suppression, regression, or partial or complete disappearance of a pre-existing cancer or tumor. The definition is meant to include any diminution in the size, potency or growth rate of a pre-existing cancer or tumor.

As used herein, the terms "improved therapeutic outcome" and "enhanced therapeutic efficacy", relative to cancer refers to a slowing or diminution of the growth of cancer cells or a solid tumor, or a reduction in the total number of cancer cells or total tumor burden. An "improved therapeutic outcome" or "enhanced therapeutic efficacy" means there is an improvement in the condition of the individual according to any clinically acceptable criteria, including reversal of an established tumor, an increase in life expectancy or an improvement in quality of life.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4 acetylcytosine, 8-hydroxy-N6-methyladenosine, aziridinylcytosine, pseudoisocytosine, 5 (carboxyhydroxyl¬methyl) uracil, 5-fluorouracil, 5 bromouracil, 5-carboxymethylaminomethyl 2 thiouracil, 5 carboxymethyl¬aminomethyluracil, dihydrouracil, inosine, N6 isopentenyladenine, 1 methyladenine, 1-methylpseudo¬uracil, 1 methylguanine, 1 methylinosine, 2,2-dimethyl¬guanine, 2 methyladenine, 2 methylguanine, 3-methyl¬cytosine, 5 methylcytosine, N6 methyladenine, 7 methylguanine, 5 methylaminomethyluracil, 5-methoxyamino¬methyl 2 thiouracil, beta D mannosylqueosine, 5' methoxycarbonylmethyluracil, 5 methoxyuracil, 2 methylthio N6 isopentenyladenine, uracil 5 oxyacetic acid methylester, uracil 5 oxyacetic acid, oxybutoxosine, pseudouracil, queosine, 2 thiocytosine, 5-methyl-2 thiouracil, 2-thiouracil, 4 thiouracil, 5-methyluracil, N-uracil 5 oxyacetic acid methylester, uracil 5 oxyacetic acid, pseudouracil, queosine, 2-thiocytosine, and 2,6 diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc.). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "transgene" refers to a heterologous gene that is integrated into the genome of an organism (e.g., a non-human animal) and that is transmitted to progeny of the organism during sexual reproduction.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post transcriptional cleavage and polyadenylation.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

"Sequence identity," "% sequence identity" and the like with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors of utility in recombinant DNA techniques are often in the form of plasmids. In the present specification, "plasmid" and "vector" may be used interchangeably as the plasmid is the most commonly used form of vector.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher (or greater) than that observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA. The term "transient transfection" or "transiently transfected" refers to the introduction of foreign DNA into a cell where the foreign DNA fails to integrate into the genome of the transfected cell. The foreign DNA persists in the nucleus of the transfected cell (e.g., for several days). During this time the foreign DNA is subject to the regulatory controls that govern the expression of endogenous genes in the chromosomes. The term "transient transfectant" refers to cells that have taken up foreign DNA but have failed to integrate this DNA.

As used herein, the term "selectable marker" refers to the use of a gene that encodes an enzymatic activity that confers the ability to grow in medium lacking what would otherwise be an essential nutrient; in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk-cell lines, the CAD gene that is used in conjunction with CAD-deficient cells and the mammalian hypoxanthine-guanine phosphoribosyl transferase (hprt) gene that is used in conjunction with hprt-cell lines. A review of the use of selectable markers in mammalian cell lines is provided in Sambrook, J. et al., Molecular Cloning: A Laboratory Manual, 2nd ed., Cold Spring Harbor Laboratory Press, New York (1989) pp. 16.9-16.15.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used herein, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

DETAILED DESCRIPTION OF THE INVENTION

The present invention relates to the treatment of cancer and to the prevention of cancer growth and/or metastasis. In particular, the invention relates to cellular and acellular immunogenic compositions (e.g., vaccines) containing C3d, a proteolytic product of complement (C3), and methods of enhancing a host immune response (e.g., a T cell mediated immune response) against cancer and/or lymphoma using the immunogenic compositions described herein. Compositions and methods of the invention find use in treating lymphoma and/or cancers that develop and/or persist by evading host immune surveillance and/or responses (e.g., T-cell mediated immune responses).

The complement immune system is an active component of innate immunity that attacks foreign pathogens by covalently attaching to antigenic targets of pathogens, lysing pathogen surface membranes, and via initiation of inflammatory responses. Complement activation leads to the formation of B-cell co-receptor complexes, thereby linking innate and adaptive immune responses. Activation of complement has long been thought to integrate innate and adaptive immunity, particularly humoral immunity, as the tagging of antigen with fragments of C3 initiate B cell responses when antigen is limiting (See, e.g., Dempsey et al., Science 271, 348-350 (1996)). Absence or depletion of C3 does impair T cell responses to influenza (See, e.g., Kopf et al., Nature medicine 8, 373-378 (2002), auto-antigens (See, e.g., Kaya et al., Nature immunology 2, 739-745 (2001) and alloantigens (See, e.g., Pratt et al., Nature medicine 8, 582-587 (2002); e.g., Liu et al., The Journal of experimental medicine 201, 567-577 (2005); and Heeger et al., The Journal of experimental medicine 201, 1523-1530 (2005)); but, how C3d might help initiate and control T cell responses beyond facilitating antigen presentation when bound to immune-complexes is not known.

Most C3d generated during tissue injury and infection is not associated with immunogenic proteins (e.g., covalently attached to antigenic targets) and little is known about how this C3d, in a free state or associated with self antigens, might impact, if at all, the inception of protective immune responses.

Experiments conducted during development of embodiments of the invention identified a surprising and distinct, active role for C3d in the treatment and prevention of cancer. For example, the present invention provides an immunogenic composition comprising cancer cells modified to express or harbor C3d (e.g., cancer cells genetically modified to express C3d as a monomer or an oligomer (e.g., C3d monomers or oligomers that are free from attachment to a specific antigen (e.g., a pathogenic antigen))) that, when administered to a subject, provokes a rapid and robust cancer-specific immune response that not only delays tumor progression, but in some embodiments, effects a cure (e.g., eradicates detectable tumor in a subject administered the immunogenic composition) (See, e.g., Examples 1 and 2, FIGS. 1 and 2). Thus, as described in detail herein, the invention provides immunostimulatory/immunogenic compositions (e.g., containing free C3d (e.g., C3d that is free from attachment to an antigen) and cancer cells and/or one or more tumor antigens) and methods of using the same (e.g., as vaccines) to stimulate tumor-specific immune responses (e.g., for therapeutic and/or prophylactic treatment of cancer (e.g., cancer immunity)).

Regulatory T cells (Tregs), formerly known as suppressor T cells, are a subpopulation of T cells that modulate the immune system, maintain tolerance to self-antigens, and abrogate autoimmune disease. Tregs are immunosuppressive, and generally suppress or down-regulate induction, proliferation, and function of effector T cells (See, e.g., Bettelli, et al., Nature 441 (7090): 235-238 (2006)). Tregs express the biomarkers CD4, FoxP3, and CD25 and are thought to be derived from the same lineage as naïve CD4 cells (See, e.g., Curiel, Journal of Clinical Investigation 117 (5): 1167-1174 (2007)). Because effector T cells also express CD4 and CD25, Tregs have been difficult to effectively discern from effector CD4+, making them difficult to study.

While an understanding of a mechanism of action is not needed to practice the present invention, and while the present invention is not limited to any particular mechanism, in one embodiment, the invention provides that administration of an immunogenic composition of the invention to a subject (e.g., a subject with cancer) reduces and/or clears (e.g., via programmed cell death) T regulatory cells (Tregs) within the subject (e.g., thereby reducing and/or eliminating T regulator cell immune suppression against the cancer) (See, e.g., Examples 1 and 2). For example, in one embodiment, administration of an immunogenic composition of the invention to a subject (e.g., a subject with cancer) results in a detectable level of T regulator cells expressing caspase 3 and/or caspase 7 (e.g., indicating that the cells have been targeted for and/or are undergoing apoptosis).

In another embodiment, administration of an immunogenic composition of the invention to a subject (e.g., a subject with cancer) results in a detectable, reduced number of tumor cells in the subject. While an understanding of a mechanism of action is not needed to practice the present invention, and while the present invention is not limited to any particular mechanism, in one embodiment, the invention provides that administration of an immunogenic composition of the invention to a subject (e.g., a subject with cancer) stimulates anti-tumor immunity by suppressing expression of PD-1, a powerful inhibitor of anti-tumor immunity (e.g., leading to apoptosis of Tregs). Accordingly, in embodiments in which C3d is associated with tumor cells and/or a tumor cell vaccine, the invention provides a significant advantage in that it avoids pleiotropic effects complement exerts and the systemic toxicity associated with generalized inhibition of PD-1 and PD-L1 (See, e.g., Kolev et al., Immunity 42, 1033-1047 (2015); Postow et al., Journal of clinical oncology: official journal of the American Society of Clinical Oncology 33, 1974-1982 (2015); Naidoo et al., Annals of oncology: official journal of the European Society for Medical Oncology/ESMO 26, 2375-2391 (2015)).

Figure 3A:
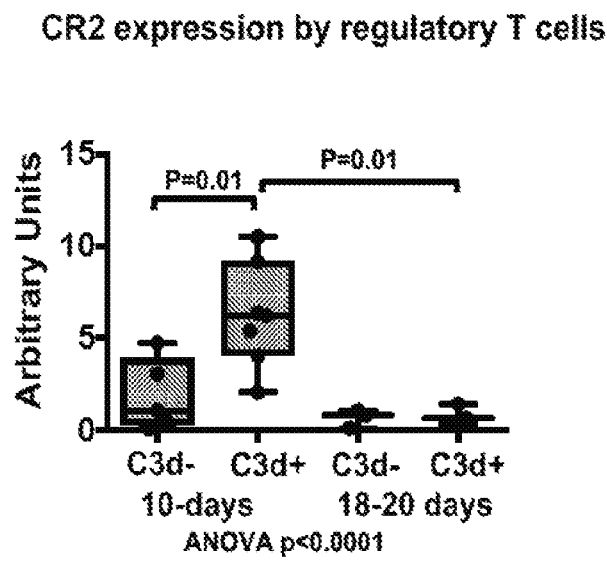
FIG. 3 shows the impact of C3d on expression of CR2 (CD21) by regulatory T cells (Treg) and on apoptosis of Treg and CD8+ cells in lymphomas. (A) CR2 expression, by Treg after introduction of C3d+ or C3d− lymphoma cells. Expression was determined by qPCR relative to GAPDH, CR2 expression by naïve T regulatory cells was subtracted. (B and F) Frequency of CD21+ Treg determined by flow cytometry analysis of splenocytes. (C and G) Expression of CR2 (CD21) and caspase-3 and -7 in T regulatory cells (CD4+, Foxp3+), assayed by flow cytometry, in mice injected with C3d+ or C3d− lymphoma cells 10 days before. The graphs depict frequencies of apoptotic regulatory T cells in tumor-recipient mice. (D) Frequency of T regs (CD4+, Foxp3+) determined by flow cytometry, 18 days after tumor transfer. (E) Immunofluorescence analysis of frozen sections of C3d+ or C3d− lymphoid tumors stained with anti-Foxp3 antibodies. (H and I) Expression of caspase-3 and -7 in CD8+ T cells assayed by flow cytometry, in mice injected with C3d+ or C3d− lymphoma cells 10 days before. Flow cytometry graphs reflect analysis of splenocytes in mice for each condition. Boxes represent distribution of data between the 25 and the 75 percentiles. The mean is indicated by a horizontal line and whiskers represent maximum and minimum values. Statistical analysis in A and B was by the Kruskal Wallis test followed by Dunns multiple comparison test. Analysis in C, D and I was by the Mann-Whitney 2 tailed test.
Figure 3B:
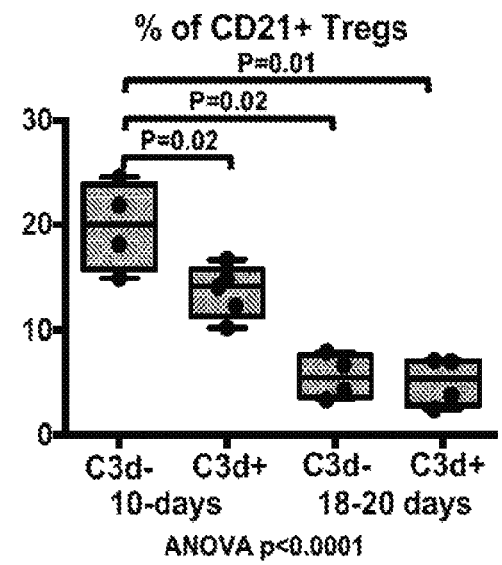
Figure 3C:
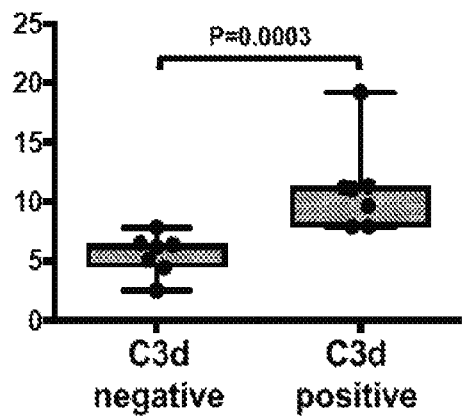
Figure 3D:
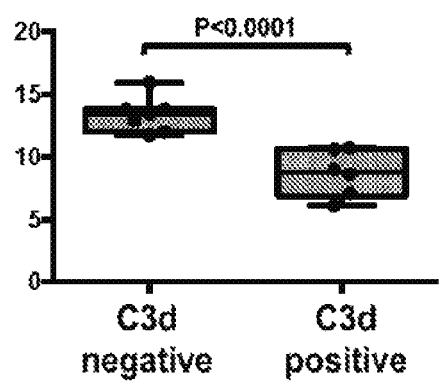
Figure 3E:
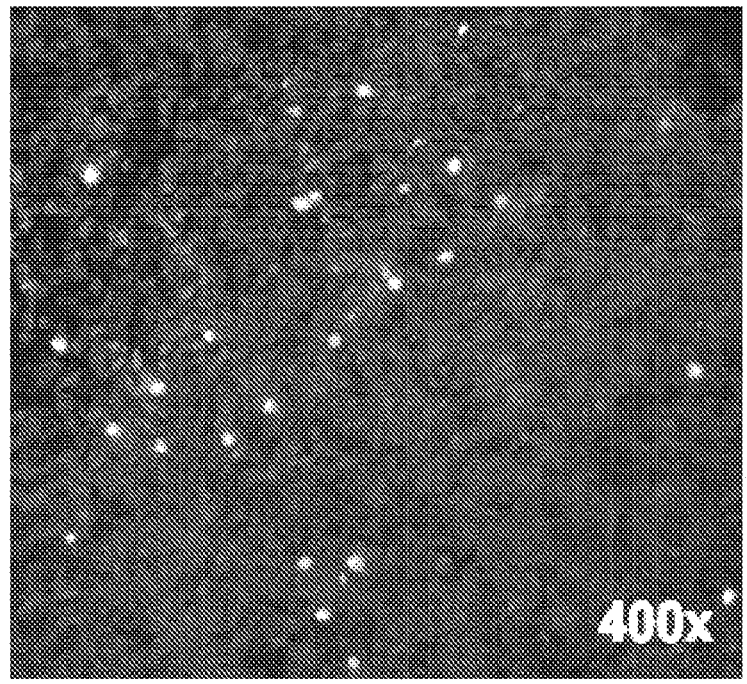
Figure 3E:
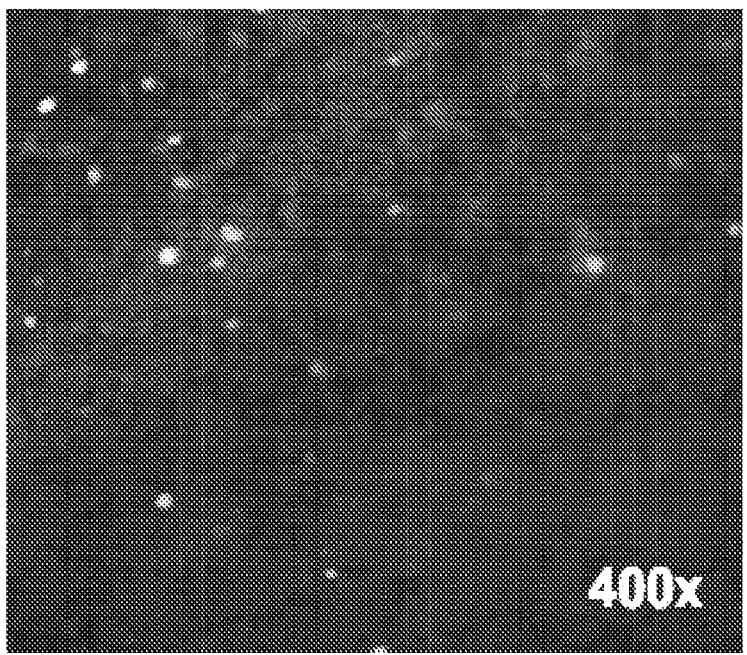

In another embodiment, the invention provides that administration of an immunogenic composition of the invention to a subject (e.g., a subject with cancer) increases the number and/or frequency of T cells (e.g., tumor-specific T cells) producing perforin, TNF-alpha and/or interferon γ (See, e.g., Example 2, FIGS. 3E and 3F) that exhibit cytotoxicity for tumor cells (See, e.g., Example 2, FIG. 3D). In yet another embodiment, the invention provides that administration of an immunostimulatory/immunogenic composition of the invention to a subject (e.g., a subject with cancer) increases the engagement of and signaling via complement receptor 2 (CR2) (e.g., thereby resulting in increased survival of subjects administered the immunogenic composition (See, e.g., Example 2, FIG. 4B).

The invention provides compositions (e.g., immunogenic compositions) and methods of using the compositions (e.g., methods of administering the compositions (e.g., as a vaccine)) to generate an immune response to cancer in a subject. The invention provides, in one embodiment, an immunogenic composition that is cell based comprising cancer cells modified (e.g., genetically engineered) to express C3d. In another embodiment, the composition is a cell based composition comprising cancer cells administered with isolated (e.g., recombinant) C3d. In still another embodiment, the composition is a cell based composition comprising cancer cells and further including one or more cell line(s) modified (e.g., genetically) to express C3d. In one embodiment, a cell based immunogenic composition comprises inactivated (e.g., irradiated) cancer cells (e.g., irradiated, whole cancer cells modified to express C3d). The invention is not limited by the means of inactivating cancer cells. Indeed, any method known in the art may be used including those described herein.

Immunogenic compositions of the invention that are cell based (e.g., comprising cancer cells (e.g., modified (e.g., genetically engineered) to express or to harbor C3d)) are not limited to any specific cell population. Indeed, a variety of different types of cells may be used including, but not limited to, unmodified tumor cells, tumor cells or non-tumor cells modified to express C3d, tumor cells or non-tumor cells modified to express one or more tumor antigens, and tumor cells or non-tumor cells modified to express C3d and one or more tumor antigens. In one embodiment, a cell based immunogenic composition of the invention is inactivated (e.g., prior to administration to a subject). The invention is not limited by the method or mechanism of inactivation of cells used in a cell based immunogenic composition of the invention. Indeed, methods of cell inactivation are well known by those of skill in the art and any such method may be used. In one embodiment, cells are inactivated using irradiation.

In one embodiment, for cells that have been modified (e.g., genetically modified), following culture of the cells and prior to administration to a subject (e.g., as a vaccine or immunotherapeutic), the cells are processed to remove components used in preparing the cells. For example, culture serum (e.g., fetal calf serum, bovine serum, etc.) components, or other biological supplements in the culture medium are removed. In one embodiment, the cells are washed (e.g., using repeated centrifugation) into a suitable pharmacologically compatible excipient. The invention is not limited by the type of pharmacologically acceptable excipient used. As described herein, exemplary compatible excipients include, but are not limited to, isotonic saline, with or without a physiologically compatible buffer like phosphate or Hepes and nutrients such as dextrose, physiologically compatible ions, or amino acids, and various culture media (e.g., those devoid of immunogenic components).

In another embodiment, the invention provides an immunogenic composition comprising an antigen (e.g., cancer or tumor cells or recombinant and/or isolated tumor antigen) modified (e.g., genetically engineered) to express C3d.

In another embodiment, the invention provides an immunogenic composition comprising an antigen (e.g., an oncogenic microbe (e.g., a pathogen or pathogen product that causes cancer)) and C3d. For example, an immunogenic composition of the invention may comprise an oncogenic microbe, or an antigenic component thereof, and C3d. Alternatively, an immunogenic composition may comprise an oncogenic microbe, or an antigenic component thereof, and a cell line modified to express or to harbor C3d. The invention is not limited by the oncogenic microbe. Exemplary oncogenic microbes include, but are not limited to, Epstein Barr Virus (EBV), hepatitis B virus (HBV), hepatitis C virus (HCV), human herpes virus (HHV), human papilloma virus (HPV), *Helicobacter pylori*, HTLV-1, *Schistosoma haematobium*, and *Clonorchis sinensis*. In another embodiment, the invention provides a method of inhibiting suppression of immunity (e.g., cellular immunity) and/or immune responses against an oncogenic microbe in a host comprising administering to the host an immunogenic composition comprising an antigen (e.g., an oncogenic microbe (e.g., a pathogen or pathogen product that causes cancer)) and C3d.

In another embodiment, the immunogenic composition comprises one or more tumor antigens (e.g., recombinant and/or isolated tumor antigens) and also includes C3d (e.g., recombinant and/or isolated C3d. In still a further embodiment, the immunogenic composition comprises one or more tumor antigens (e.g., recombinant and/or isolated tumor antigens) and also includes a cell line(s) (e.g., a cancer cell line or a non-cancer cell line) modified to express C3d.

In one embodiment, the invention provides an immunogenic composition comprising a cell lysate harvested from cancer cells expressing C3d. In another embodiment, the immunogenic composition comprises a cell lysate from cancer cell expressing C3d and also includes cancer cells (e.g., killed cancer cells). In another embodiment, the immunogenic composition comprises a cell lysate from cancer cells expressing C3d, further includes cancer cells, and also includes isolated (e.g., recombinant) C3d.

The invention also provides methods of manufacturing any one of the immunogenic compositions, or a combination thereof, described herein.

The present invention is not limited by the type of cancer and/or tumor (e.g., utilized in an immunogenic composition of the invention and/or treated with an immunogenic composition of the invention). Indeed, any cancer or tumor may be used and/or treated including, but not limited to, cancer of the bladder, breast, colon, kidney, liver, lung, ovary, cervix, pancreas, rectum, prostate, stomach, epidermis; a hematopoietic tumor of lymphoid or myeloid lineage (e.g., leukemias, myelomas, and lymphomas); a tumor of mesenchymal origin such as a fibrosarcoma or rhabdomyosarcoma; other tumor types such as melanoma, teratocarcinoma, neuroblastoma, glioma, adenocarcinoma and non-small lung cell carcinoma.

The invention is not limited by the means in which cells (e.g., autologous and/or allogeneic tumor/cancer cells) are modified to express and/or harbor C3d or other agent. For example, in one embodiment, a tumor cell is modified to express C3d via introduction of nucleic acid sequence encoding C3d (e.g., thereby leading to expression of C3d in the cell). In a preferred embodiment, C3d expressed or harbored in a cell is free C3d (e.g., C3d polypeptide or oligomers of C3d polypeptide that are not part of a chimeric molecule encoding one or more specific antigens (e.g., pathogenic antigens (e.g., hemagglutinin of influenza virus, autolysin of *Staphylococcus aureus*, etc.))). C3d utilized in the invention may be human C3d, non-human primate C3d, murine C3d, or other available C3d sequence. In one embodiment, all or a portion of the nucleic acid sequence of SEQ ID NO: 1, SEQ ID NO: 3, and/or SEQ ID NO: 5 (e.g. shown in FIG. 8) is used to express C3d (e.g., using an expression vector to express C3d in vivo or in vitro). In a further embodiment, an immunostimulatory fragment of C3d is used. For example, in some embodiments, any fragment of C3d that is immunostimulatory (e.g., that activates complement receptor 2 (CR2)) finds use in the compositions and methods of the invention. The invention is not limited to any particular fragment of C3d. Indeed, multiple fragments of C3d are known to be immunostimulatory (e.g., activate CR2) including, but not limited to, a 28 amino acid peptide of C3d (P28) (See, e.g., Lambris et al. Proc Natl Acad Sci, 82:4235-4239 (1985); Servis and Lambris, J Immunol, 142: 2207-2212 (1989)) as well as a 16 amino acid peptide (p16) of C3d (See, e.g., Lyamani et al., Biochem Biophys Res Comm 175:823-830 (1991)). Additional fragments of C3d can be assessed and identified as immunostimulatory (e.g., able to activate CR2) using methods well known to those in the art (e.g., methods described herein) and these fragments also find use in the compositions and methods of the invention. Indeed, any C3d peptide, or fragment thereof, that is immunostimulatory (e.g., that binds to CR2 and/or stimulates CR2 activity) finds use in the compositions and methods of the invention. For example, in some embodiments, C3d, or an immunostimulatory fragment thereof, comprises an amino acid sequence having at least 75%, 80%, 85%, 90%, 95%, 97%, 98%, 99% or more sequence identity to the entire amino acid sequence of SEQ ID NO: 2, SEQ ID NO: 4 or SEQ ID NO: 6 (e.g., shown in FIG. 9), or to a fragment thereof (e.g., a 16-30 amino acid fragment, a 30-100 amino acid fragment, a 100-200 amino acid fragment, a 200-300 amino acid fragment or longer fragment of SEQ ID NO: 2, 4 or 6 having at least 75%, 80%, 85%, 90%, 95%, 97%, 98%, 99% or more sequence identity to the corresponding amino acid sequence of SEQ ID NO: 2, SEQ ID NO: 4 or SEQ ID NO: 6). The invention is not limited to any particular fragment of C3d. Indeed, any fragment of C3d that is known to be or identified to be (e.g., using compositions and methods described herein and/or known in the art) immunostimulatory (e.g., activate CR2) can be used.

In some embodiments, full length C3d, or an immunostimulatory fragment thereof, is co-administered with a one or more other CR2 agonists (e.g., to induce an immune response (e.g., to reduce immune tolerance and to induce an immune response (e.g., to stimulate and/or induce an anti-cancer immune response (e.g., a T cell mediated anti-cancer immune response))). The invention is not limited to any particular CR2 agonist. Indeed, any CR2 agonist known in the art may be used including, but not limited to, anti-CR2 agonist antibody (e.g., those described herein).

Any expression vector system known in the art may be utilized for expression of a C3d nucleic acid sequence (e.g., encoding full length C3d, an immunostimulatory fragment thereof, and/or dimer, trimer, tetramer, or higher order oligomer complexes thereof) in a tumor/cancer cell. In one embodiment, a vector comprising a nucleic acid sequence encoding C3d, operably linked to a promoter and expression/control sequences necessary for expression thereof is used. C3d nucleic acid sequence may comprise the entire coding sequence or any portion thereof that encodes an immunostimulatory/immunogenic epitope thereof. C3d expressed or harbored in a cell may comprise the entire C3d polypeptide or any portion thereof capable of allowing a cancer specific immune response to occur that would otherwise not occur in the absence of the C3d polypeptide (e.g., identified and/or determined using compositions and methods disclosed herein (e.g., in Examples 1 and 2)). C3d may be expressed or present as a monomer, dimer, trimer, tetramer, or higher order oligomer complexes (e.g., 5, 6, 7, 8, 9, 10, 12, 15, 20, 25, 30 or more). For example, in one embodiment, all or a portion of the nucleic acid sequence of FIG. 8 is used to introduce C3d into tumor/cancer cells (e.g., for expression of a C3d monomer, dimer and/or trimer therein). Any expression construct available in the art may be used to express C3d in cells including those described herein (See, e.g., Example 1).

In another embodiment, cells (e.g., cancer cells (e.g., allogenic cells or autologous cells or cell lines) are modified to harbor C3d via conjugation of all or a portion of C3d (e.g., C3d monomer, dimer, trimer or higher order complex) to a protein transduction domain (PTD) and/or cell penetrating peptide (CPP) (e.g., so as to avoid introduction of foreign genetic material into the cells). The present invention is not limited by the type of PTD or CPP used. Indeed, any PTD or CPP known in the art can be used including, but not limited to, tissue-specific and non-tissue specific peptides including cationic peptides (e.g., of 6-12 amino acids in length comprised predominantly of arginine, ornithine and/or lysine residues); hydrophobic peptides (e.g., leader sequences of secreted growth factors or cytokines) and amphipathic peptides or cell-type specific peptides (e.g., obtained by linking hydrophobic peptides to nuclear localizing signals and/or identified via screening of peptide phage display libraries). PTDs and CPPs known in the art are described in Zahid and Robbins, Molecules 2015, 20(7), 13055-13070, hereby incorporated by reference in its entirety.

In one embodiment, an immunogenic composition (e.g., immunotherapeutic composition) of the invention is used in combination with, preceding, following, or in lieu of other treatments and/or therapies for treating and/or preventing cancer (e.g., preventing new cancer and/or the spread of cancer). For example, a subject to whom an immunogenic composition of the invention is administered may be treated (e.g., previously, concurrently, or subsequently) with surgical intervention, chemotherapy, radiation therapies and/or other forms of immunotherapy that are commonly used and well known in the art to treat cancer in the subject (e.g., the type of cancer a subject administered the composition of the invention has). In a further embodiment, when used, these other treatments and/or therapies are utilized in such a way (e.g., at a time or for a duration of time) that does not interfere with the efficacy of the compositions of the present invention (e.g., to inhibit cancer growth and/or to reduce or eliminate cancer cells in the subject).

In yet another embodiment, one or more compositions or methods of the invention are utilized as or in a test to determine whether a patient with a particular cancer has the capacity to mount an immune response to their cancer. For example, in one embodiment, compositions and methods of the invention are used to identify a cancer patient that possesses an immune system that is competent and/or has the capacity to recognize tumor and/or cancer cells. For example, a patient may be administered a composition of the invention (e.g., C3d plus tumor and/or cancer cells) and the immune response of the patient characterized in order to determine if the patient's immune system recognizes and/or initiates an immune response against the composition. In some embodiments, such a test (e.g., a test or assay to identify if a cancer patient possesses an immune system that is competent and/or has the capacity to recognize tumor and/or cancer cells) is used by a practitioner to identify a patient as being a candidate or not being a candidate for other types of cancer therapy (e.g., other immunotherapies, radiotherapy, chemotherapy, surgery, etc.). Thus, the invention provides one or more tests to determine if a patient will or will not respond to immunotherapy by C3d compositions and methods of the invention, or other form of immunotherapy. For example, compositions and methods of the invention can be used to identify a patient that does not have the ability to respond to an immunogenic composition of the invention (e.g., C3d plus tumor or cancer cells), thereby identifying a patient that is a candidate for a different cancer therapy (e.g., other immunotherapy (e.g., a therapy in which a patient's T cells are engineered to have a novel anti-cancer receptor (e.g. Car T cell therapy), radiotherapy, chemotherapy, surgery, etc.).

An immunotherapeutic composition of the invention may be co-administered with one or more cancer therapeutic agents. For example, an immunogenic composition of the invention may be administered with one or more cancer therapeutic agents including, but not limited to, alkylating agents, alkaloids; antimetabolites, anti-tumor antibiotics, nitrosoureas, hormonal agonists/antagonists and analogs, immunomodulators, photosensitizers, and enzymes. For example, the cancer therapeutic agent may be one or more of Docetaxel, Alkyl Sulfonates, Aclacinomycins, Folic Acid, L-Asparaginase, Interferon-α (TAXOTERE) Analogs, Etoposide, Busulfan, Actinomycin $F_1$, Denopterin, Pegasargase, Interferon-β, Irinotecan, Improsulfan, Anthramycin, Edatrexate, Interferon-γ, Paclitoxel, Piposulfan, Azaserine, Methotrexate, Interferon-α (TAXOL) 2a, Teniposide, Bleomycins, Piritrexim, Interleukin-2, Topotecan, Aziridines, Cactinomycin, Pteropterin, Lentinan, Vinblastine, Benzodepa, Carubicin, TOMUDEX, Propogermanium, Vincristine, Carboquone, Carzinophilin, Trimetrexate, PSK, Vendesine, Meturedepa, Chromomycins, Roquinimex, Vinorelbine, Uredepa, Dactinomycin, Purine Analogs, Rituximab, Daunorubicin, Cladribine, Sizofiran, Ethylenimines 6-Diazo-5-oxo-L-Fludarabine, Trastuzumab, norleucine, Methylmelamines, Altretamine, Doxorubicin 6-Ubenimex, Mercaptopurine, Triethylenemelamine, Epirubicin, Thiamiprine, Cyclophosphamide/Cytoxan, Triethylenephosphoramide, Idarubicin, Thioguanine, Triethylenethiophosphoramide, Menogaril, Mitomycins, Mitoxantrone, Pyrimidine Analogs, Nitrogen Mycophenolic Acid, Ancitabine Mustards, Chlorambucil, Nogalamycin, 5-Azacytidine, Chlomaphazine, Olivomycins, 6-Azauridine, Cyclophosphamide, Peplomycin, Carmofur, Estramustine, Pirarubicin, Cytarabine, Ifosfamide, Plicomycin, Doxifluridine, Mechlorethamine, Porfiromycin, Emitefur, Mechlorethamine, Puromycin, Enocitabine, Oxide Hydrochloride, Melphalan, Streptonigrin, Floxuridine, Novembichin, Streptozocin, Fluorouracil, Valrubilcin, Perfosfamide, Tubercidin, Gemcitabine, Phenesterine, Zinostatin, Tegafur, Prednimustine, Zorubicin, Trofosfamide, Uracil, Mustard, Carboplatin, Cisplatin, Miboplatin, Oxaliplatin, Dacarbazine, Mannomustine, Mitobronitol, Mitolactol, Thiotepa, Pipobroman, Temozolomide, Carmustine Aceglatone, Dexamethasone, Porfimer, Sodium Chlorozotocin, Amsacrine, Prednisone, Fotemustine, Bisantrene, Lomustine, Defosfamide, Androgens, Nimustine, Demecolcine, Calusterone, Ranimustine, Diaziquone, Dromostanolone, Eflornithine, Epitiostanol, Elliptinium, Mepitiostane, Acetate, Etoglucid, Testolactone, Fenretinide, Finasteride, Antiadrenals, Gallium, Nitrate, Aminoglutethimide, Hydroxyurea, Mitotane, Lonidomine, Trilostane, Miltefosine, Mitoguazone, Antiandrogens, Mopidamol, Bicalutamide, Nitracrine, Flutamide, Pentostatin, Nilutamide, Phenamet, Podophyllinic, Antiestrogens, Acid 2-Ethylhydrazide, Procarbazine, Droloxifene, Razoxane, Tamoxifen, Sobuzoxane, Toremifene, Spirogermanium, Exemestane, Amsacrine, Aromatase Inhibitors, Tretinoin, Aminoglutethimide, Tenuazonic Acid, Anastrozole, Triaziquone, Fadrozole 2,2',2"-Formestane, Triclorotriethylamine, Urethan, Letrozole, Topotecan, Estrogens, Fosfestrol, Hexestrol, Polyestradiol, Phosphate LHRA Analogs, Buserelin, Goserelin, Leuprolide, Triptorelin, Progestogens, Chlormadinone Acetate, Medroxyprogesterone, Megestrol Acetate, and/or Melengestrol The invention provides methods of using one or more of the immunogenic compositions of the invention for treating (e.g., therapeutically and/or prophylactically) cancer in a patient. For example, in one embodiment, the invention provides a method of treating a patient with cancer comprising administering a therapeutically effective amount (e.g., an amount sufficient to induce a cancer specific immune response) of an immunogenic composition of the invention to the subject (e.g., that induces a cancer specific immune response in the subject). The invention is not limited by the type of cancer treated. Similarly the invention is not limited by the immunogenic composition utilized. Indeed, any immunogenic composition and/or cancer described herein may be used and/or treated. Subsequent to administration of an immunogenic composition of the invention to a patient, one or more immune responses to the cancer (e.g., cancerous tissue (e.g., tumor) or cells is detected (e.g., wherein the one or more immune responses are not detected in the patient prior to administering the immunogenic composition). The invention is not limited by the type of immune response detected. Indeed, any type of immune response described herein that is specific for the cancer may be detected. In a preferred embodiment, the response detected comprises a detectable, reduced number of tumor cells in the patient. In another preferred embodiment, the response detected comprises a reduction and/or clearance of Tregs within the patient (e.g., a detectable reduction and/or elimination of T regulator cell immune suppression against the cancer). In another preferred embodiment, the response detected comprises an increase in the level of T regulator cells expressing caspase 3 and/or caspase 7. In yet another preferred embodiment, the detected response comprises an increase in the number and/or frequency of T cells (e.g., tumor-specific T cells) expressing and/or producing perforin, TNF-alpha and/or interferon γ (e.g., increase the total number of cancer-specific, cytotoxic T cells). The present invention provides immunogenic compositions and methods of using the same (e.g., for administration to patients (e.g., as vaccines) for therapeutic and prophylactic treatment) that not only results in each of the above detectable immune responses, but also provides increased survival rates for patients with cancer (e.g., compared to patients not receiving the immunogenic compositions).

The invention also provides that, subsequent to detecting the one or more immune responses in the patient, treatment of the patient is modified (e.g., increased (e.g., the amount of cancer specific treatment (e.g., radiation, chemotherapy, surgical intervention) is augmented); decreased (e.g., the amount of cancer specific treatment (e.g., radiation, chemotherapy, surgical intervention) is reduced) and/or one or more additional treatments (e.g., the amount of cancer specific treatment (e.g., radiation, chemotherapy, surgical intervention) are started or discontinued (e.g., based on the status of the immune response(s) detected in the patient).

Thus, as described herein, the present invention provides a method of stimulating an immune response to cancer in a subject. Desirably, the method effects a systemic immune response (e.g., a T-cell response and/or a B-cell response) to the cancer. The method comprises administering to the patient an immunogenic composition comprising C3d and a tumor or cancer antigen. In a preferred embodiment, the immunogenic composition comprises a cancer or tumor cell that has been modified to express C3d. In a further preferred embodiment, the cells are treated prior to administration to a patient so as to be proliferation incompetent (e.g., via irradiation). In a further preferred embodiment, a therapeutically effective amount of the immunogenic composition is administered to the subject/patient. Upon administration of the composition, an immune response to the cancer is elicited or enhanced. In one approach, the immunogenic composition (e.g., vaccine) comprises a single population of cells that is modified to express C3d. In another approach, the immunogenic composition comprises two or more populations of cells individually modified to express C3d. In another embodiment, the immunogenic composition is administered in combination with at least one other cancer therapeutic agent or treatment (e.g., one disclosed herein). In one embodiment, the immunogenic composition of the invention comprises cancer/tumor cells selected from autologous cells, allogeneic cells, and/or a tumor cell line. The invention is not limited by the time the cells are used (e.g., post isolation and/or modification of the cells). Indeed, the cells may be used within hours, days, weeks months or years. The cells may be preserved (e.g., cryopreserved or preserved in media) (e.g., prior to administration to a patient in need thereof).

In one embodiment, cells of an immunogenic composition of the invention are administered to the same individual from whom they were derived (autologous). In another embodiment, cells of an immunogenic composition of the invention are administered to a different individual(s) from whom they were derived (allogeneic or tumor cell line (e.g., bystander cell)). In one embodiment, cells of an immunogenic composition of the invention comprise cells modified to express C3d and cells modified to express one or more tumor antigens and/or cells modified to express one or more cancer therapeutic agents. In still another embodiment, cells of an immunogenic composition of the invention comprise cells that express C3d that are autologous cells and cells that express one or more tumor antigens and/or cells modified to express one or more cancer therapeutic agents that are autologous or allogeneic cells.

Thus, in one embodiment, the invention provides a method of treating cancer in a patient in need thereof comprising the steps of: (a) obtaining tumor cells from a patient harboring a tumor; (b) modifying the tumor cells to render them capable of producing C3d (c) rendering the modified tumor cells proliferation incompetent; and (d) administering the modified tumor cells to the patient from which the tumor cells were obtained. In another embodiment, the invention provides a method of treating cancer in a patient in need thereof comprising the steps of: (a) obtaining tumor cells from a patient harboring a tumor; (b) modifying the tumor cells to render them capable of producing C3d (c) rendering the modified tumor cells proliferation incompetent; and (d) administering the modified tumor cells to a second, different patient from which the tumor cells were obtained. In one embodiment, the second, different patient comprises the same or similar MHC type (e.g., matched HLA haplotype) as the patient from which the tumor cells were obtained. In another embodiment, the second, different patient comprises a different MHC type (e.g., HLA haplotype) as the patient from which the tumor cells were obtained.

The same autologous tumor cells may be used to express both C3d and optionally a cancer therapeutic agent(s), or C3d and a cancer therapeutic agent may be expressed by different autologous tumor cell populations. The invention is not limited by the means by which cells (e.g., autologous tumor cells) are modified to express C3d or other agent. For example, in one embodiment, a tumor cell is modified by introduction of a vector comprising a nucleic acid sequence encoding C3d, operably linked to a promoter and expression/control sequences necessary for expression thereof. In another embodiment, the same autologous tumor cell is modified by introduction of a vector comprising a nucleic acid sequence encoding at least one tumor antigen or additional cancer therapeutic agent operably linked to a promoter and expression/control sequences necessary for expression thereof. In a further aspect, a second autologous tumor cell is modified by introduction of a vector comprising a nucleic acid sequence encoding at least one tumor antigen and/or additional cancer therapeutic agent operably linked to a promoter and expression/control sequences necessary for expression thereof. Nucleic acid sequences encoding C3d and/or tumor antigen(s) and/or additional cancer therapeutic agent(s) may be introduced into the same or a different autologous tumor cell using the same or a different vector (e.g., viral expression vector). Nucleic acid sequences used for modification of cells may or may not further comprise a selectable marker sequence operably linked to a promoter.

The invention also provides, in one embodiment, a method for treating cancer in a patient in need thereof by carrying out the steps of: (a) obtaining a tumor cell line: (b) modifying the tumor cell line to render the cells capable of producing and/or expression C3d relative to the unmodified tumor cell line; (c) rendering the modified tumor cell line proliferation incompetent; and (d) administering the tumor cell line to a patient having at least one tumor that is the same type of tumor as that from which the tumor cell line was obtained or wherein the tumor cell line and patient's tumor express at least one common antigen. Thus, in one embodiment, the patient comprises a different MEW type (e.g., un-matched HLA haplotype) as the patient from which the tumor cell line was obtained/derived. Methods for the production of gene-modified allogeneic cells are described for example in WO 00/72686A1, hereby incorporated by reference in its entirety.

Thus, in one embodiment, the invention provides an immunogenic composition comprising gene-modified allogeneic cells (e.g., cells (e.g., a tumor cell line) derived from a subject other than the subject being treated) into which C3d encoding nucleic acid sequences have been introduced. In another embodiment, C3d sequences are introduced into separate (e.g., different) allogeneic tumor cell lines. The cell or population of cells may be from a tumor cell line of the same type as a tumor or cancer being treated in a patient. In one embodiment, an allogeneic tumor cell is modified by introduction of a vector comprising a nucleic acid sequence encoding C3d, operably linked to a promoter and expression control sequences necessary for expression thereof. In another aspect, the same allogeneic tumor cell or a second allogeneic tumor cell is modified by introduction of a vector comprising a nucleic acid sequence encoding a tumor antigen and/or at least one cancer therapeutic agent operably linked to a promoter and expression control sequences necessary for expression thereof. The nucleic acid sequence encoding C3d and tumor antigen(s) and/or additional cancer therapeutic agent(s) may be introduced into the same or a different allogeneic tumor cell using the same or a different vector. Nucleic acid sequences used for modification of cells may or may not further comprise a selectable marker sequence operably linked to a promoter.

In another embodiment, cells (e.g., cancer cells (e.g., allogenic cells or autologous cells) or cell lines) are modified to harbor C3d via conjugation of all or a portion of C3d to a protein transduction domain (PTD) and/or cell penetrating peptide (CPP) (e.g., so as to avoid introduction of foreign genetic material into the cells). The present invention is not limited by the type of PTD or CPP used. Indeed, any PTD or CPP known in the art can be used including, but not limited to, tissue-specific and non-tissue specific peptides including cationic peptides (e.g., of 6-12 amino acids in length comprised predominantly of arginine, ornithine and/or lysine residues); hydrophobic peptides (e.g., leader sequences of secreted growth factors or cytokines) and amphipathic peptides or cell-type specific peptides (e.g., obtained by linking hydrophobic peptides to nuclear localizing signals and/or identified via screening of peptide phage display libraries). PTDs and CPPs known in the art are described in Zahid and Robbins, Molecules 2015, 20(7), 13055-13070, hereby incorporated by reference in its entirety.

In another embodiment, the invention provides an immunogenic composition comprising cells (e.g., cancer cells (e.g., allogenic cells or autologous cells) or cell lines)) into which C3d has been introduced. Any method known in the art may be used to introduce C3d into cells. In one embodiment, cells are modified to harbor C3d via conjugation of all or a portion of C3d to a protein transduction domain (PTD) and/or cell penetrating peptide (CPP) (e.g., so as to avoid introduction of foreign genetic material into the cells). The present invention is not limited by the type of PTD or CPP used. PTDs and CPPs known in the art are described in Zahid and Robbins, Molecules 2015, 20(7), 13055-13070, hereby incorporated by reference in its entirety. In one embodiment, an immunogenic composition of the invention comprises a combination of autologous and allogenic cells (e.g., those described herein). Any ratio of allogenic to autologous cells may be used. In one embodiment, the ratio of allogeneic cells to autologous cancer cells in a given administration varies depending upon the combination.

Any suitable route of administration can be used to introduce an immunogenic composition of the invention into a subject. Exemplary routes of administration include intravenous, subcutaneous or intratumor administration. Local or systemic delivery can be accomplished by administration comprising administration of the combination into body cavities, by parenteral introduction, comprising intramuscular, intravenous, intraportal, intrahepatic, peritoneal, subcutaneous, and/or intradermal administration. In the event that a tumor is in the central nervous system, the composition can be administered in the periphery to prime naive T-cells in the draining lymph nodes. The activated tumor-specific T-cells are able to cross the blood/brain barrier to find their targets within the central nervous system.

Immunogenic compositions of the invention (e.g., a pharmaceutical composition comprising an immunogenic composition and one or more pharmaceutically acceptable carriers and/or excipients) can be used to treat cancer in a subject by administering them as one or more cancer immunotherapies. Techniques for formulation and administration are known in the art and may be found in Remington's Pharmaceutical Sciences, 18th ed., Mack Publishing Co., Easton, Pa. (1990). The invention is not limited by the amount or dose of immunogenic composition. In a preferred embodiment, the amount of immunogenic composition administered is a therapeutically effective amount. An immunogenic composition of the invention may be administered as a unit dose to a subject, each unit containing a predetermined quantity (e.g., about $10^3$ to about $10^{10}$ of cells described herein (e.g., cancer cells modified to express C3d) in order to produce the desired therapeutic effect. As detailed herein, cells that are administered to a subject may be autologous and/or allogeneic (e.g., a cell line or a bystander cell).

Those of skill in the art know well how to determine optimal treatment regimens and also know that such treatment may vary from subject to subject (e.g., depending on the type and stage of disease). As a result, it will be understood that the status of a cancer patient and the general health of the patient prior to, during, and following administration of an immunogenic composition of the invention, the patient will be evaluated in order to determine if the dose and relative timing of administration should be optimized to enhance efficacy or additional cycles of administration are indicated. Such evaluation is typically carried out using tests employed by those of skill in the art to evaluate traditional cancer chemotherapy. For example, one skilled in the art is aware of means to monitor the therapeutic outcome and/or the systemic immune response upon administering an immunogenic composition of the present invention. In particular, the therapeutic outcome can be assessed by monitoring attenuation of tumor growth and/or tumor regression and/or the level of tumor specific markers. The attenuation of tumor growth or tumor regression in response to treatment can be monitored using several end-points known to those skilled in the art including, for instance, number of lymphoma, tumor mass or size, or reduction/prevention of metastasis.

The invention is further described by reference to the following examples, which are provided for illustration only. The invention is not limited to the examples, but rather includes all variations that are evident from the teachings provided herein. All publicly available documents referenced herein, including but not limited to U.S. patents are specifically incorporated by reference.

EXAMPLES

The following examples serve to illustrate certain preferred embodiments and aspects of the present invention and are not to be construed as limiting the scope thereof.

In the experimental disclosure which follows, the following abbreviations apply: eq (equivalents); µ (micron); M (Molar); µM (micromolar); mM (millimolar); N (Normal); mol (moles); mmol (millimoles); µmol (micromoles); nmol (nanomoles); g (grams); mg (milligrams); µg (micrograms); ng (nanograms); L (liters); ml (milliliters); µl (microliters); cm (centimeters); mm (millimeters); µm (micrometers); nM (nanomolar); °C. (degrees Centigrade); and PBS (phosphate buffered saline).

Example 1

Materials & Methods

Mice and Tumor Formation. Female BALB/c ($H-2^d$), C57BL/6J ($H-2^b$), and Rag2$^{-/-}$ ($H-2^d$) mice were purchased from the Jackson Laboratory (JAX; Bar Harbor, Me.). BALB/c JH$^{-/-}$κ$^{-/-}$ ($H-2^d$) mice lack mature B cells and Ig owed to gene-targeted deletion of the JH and Jκ segments and were bred at the University of Michigan. Lymphoid tumors were induced by adoptive transfer i.p. of $5\times10^3$ or $10^7$ cells, as indicated, of either pre B cell lymphoma cell lines expressing or not expressing C3d.

Whenever tumor diameter exceeded 10 mm, or whenever there were signs of excessive morbidity, animals were euthanized and the event recorded as death from tumor burden. Melanoma tumors were obtained by s.c. injection of $10^5$ B16 cells expressing or not expressing C3d, in the flank region. Tumor volumes were determined by measuring two diameters of the dissected tumors, using electronic calipers, calculating the average radius and converting to circle areas or spherical volumes.

C3d expression vectors. To generate the vector encoding expression of only the C3d gene to transfect lymphoma cells, the pcDNA3.1 vector containing the Eμ enhancers, $\lambda_1$ promoter and HIV-ENV-C3d vector was modified. Specifically, the completed vector was partially digested with Nhe1 and fully digested with BAM H1. The DNA was then separated by gel electrophoresis and the 10.7 Kb band representing the pcDNA 3.1 vector without the gp140 sequence but with the Eμ enhancer, $\lambda_1$ promoter and C3d DNA was purified from the gel. The ends of this DNA were then filled in with Klenow and ligated together to form a vector that would drive expression of only C3d by the B cell regulatory elements. The Eμ was a 678 bp sequence (NCBI #M12827 pos 7 to 683), and the $\lambda_1$p was a 1625 bp sequence (NCBI #AC140201 pos 32137 to 30517).

C3d-vector for B16-melanoma cell transduction. C3d(×3) fragment was excised from the pcDNA3.1 C3d vector by BAMH1-XHO1 digest and cloned into the BAM-H1 site of the pLentilox 3.7-puro vector obtained from the Vector Core at the University of Michigan. Positive clones were confirmed by PCR and sequencing of the insert. C3d expression is driven by the CMV promotor and enhancer. Lentiviral preps were made by the Vector Core at the University of Michigan from empty vector or from C3d encoding vector. Transduced cells (controls with empty vector or C3d expressing) were selected by puromycin resistance and C3d expression was confirmed by PCR of cDNA and by Western blot.

Western blot analysis of C3d-expression. C3d protein expression by tumor cells was determined in cell lysates obtained from cells grown to approximately $10^6$ cells per ml in 20 ml media. Cells were lysed with RIPA Lysis Buffer supplemented with a cocktail of protease inhibitors, PMSF in DMSO and Sodium Orthovanadate in water (Santa Cruz Biotechnology, CA). Protein amount in the lysates was measured by spectrophotometry using the Pierce Microplate BCA Protein Assay Kit (Pierce Biotechnology, Thermo Scientific, IL). Cell lysates were pre-cleared by centrifugation (12,000×g, 15 minutes), separated by SDS PAGE of 5 to 20 μg of cell lysate, under reducing conditions, on 7.5% Tris-HCl READY GELs (Bio-Rad, Hercules, Calif.) followed by transfer to an Immobilon PVDF membrane (Millipore, Billerica, Mass.). On the blots, C3d was detected using goat anti-murine C3d antibody (R&D systems, Minneapolis, Minn.) (1:1000) followed by rabbit anti-goat IgG-HRP (Novus Biologicals, Littleton, Colo.).

Pathology, immunohistochemistry and immunofluorescence. Fresh tumors were harvested in linear growth phase (~600 mm³) embedded in Optimal Cutting Temperature (OCT) Compound (Tissue-Tek, CA, USA) and snap frozen. 5 μm cryo-sections were processed and after fixation, the slides were incubated with primary antibodies: goat anti-mouse C3d (15 μg/ml, R&D Systems, Minneapolis, Minn.), rat anti-mouse CD4 (GK1.5, 1:100, BD biosciences, San Jose, Calif.), rat anti-mouse CD8 (53-6.7, 1:100, BD biosciences, San Jose, Calif.), and FoxP3 (Rabbit Polyclonal; Novus Biologicals), for 2 hours at room temperature followed by Rat CF488a or Goat CF555 (Sigma) donkey secondary anti-goat IgG-AP (1:200, Southern Biotech, Birmingham, AB) incubated for 1h at room temperature.

For unequivocal identification of transgenic C3d expression in sections, tumor cells were transfected with a C3d-HIV-ENV chimera. In tumor sections, the ENV protein was detected by immunofluorescence with human HIV Immunoglobulin (HIVIg) (NIH AIDS Research & Reference Reagent Program Division of AIDS, NIAID, NIH: from NABI and National Heart Lung and Blood Institute; diluted 1:3000 to 1:5000) followed by goat anti-human, FITC-conjugated (Southern Biotech, Birmingham, AB; diluted 1:50). Sections were counterstained with a rat anti-mouse B220 antibody (RA3-6B2, BD biosciences, San Jose, Calif.) followed by goat anti-rat IgG F(ab)² rhodamine conjugated (Jackson ImmunoResearch, West Grove, Pa.; diluted 1:100).

Secondary only stained control slides had no specific staining. Imaging was performed with a Leica DMI6000B microscope using a MicroPublisher 3.3RTV camera. For each mouse, three images were taken at 400× magnification, focusing on the tumor and adjacent stroma. Each section was systematically photographed in neighboring 100× fields such that 80-100% of each tumor section was photographed. Total stain area/low power field as defined by pixel area and hue, was assessed using Q Capture Pro Imaging software (Surrey, BC, Canada).

Antibodies for Cell Depletion and Receptor/Ligand Blockade. T cells were depleted with anti-CD4 plus anti-CD8 mAb (Gk1.5 mAb (anti-CD4), 300 μg/kg of body weight plus 53-6.7 mAb (anti-CD8), 600 μg/kg of body weight, eBioscience, San Diego, Calif.)). Antibodies were given i.p. one day before and every day after tumor transfer ($5 \times 10^3$ cells), for the first two weeks, and every other day afterwards until euthanasia. Mice in control groups received injections of isotype control immunoglobulin. To test whether C3d and engagement of CR2 potentiate each other in inducing tumor regression, mAb anti-CR2/CR1 (mAb 7G6, eBioscience, San Diego, Calif.), 300 μg/kg g of body weight, was administered 1 day before and every day after tumor transfer ($5 \times 10^3$ cells), for two weeks. C3d blockade was achieved with 800 μg of soluble CR2-IgG1 (sCR2-IgG1) or IgG1 isotype control in PBS, administered i.v, 24 hours before inoculation of $10^7$ tumor cells.

Flow Cytometry and Antibodies. Single-cell suspensions were obtained from spleens and lymphoma 10 days or 18-20 days after tumor inoculation. Cells were counted and stained with allophycocyanin (APC)-conjugated monoclonal antibodies (mAbs) to either CD4 (GK1.5), CD8 (53-6.7), CD19 (ID3); phycoerythrin (PE)-conjugated mAbs to CD21/CD35 (7G6) and to PD1 (RMPI-30) purchased from BD biosciences, San Jose, Calif.; phycoerythrin (PE)-conjugated mAbs to Foxp3 (FJK-165) and Fluorescein isothiocyanate (FITC)-conjugated, Foxp3 (FJK-165) purchased from eBioscience, San Diego, Calif.; PE/Cy7-conjugated CR2/CR1 (7E9) purchased from BioLegend, San Jose Calif. Intracellular staining followed cell surface staining and was performed using a permeabilization and fixation kit, according to the manufacturer's instructions (eBioscience, San Diego, Calif.). Intra-cytoplasmic cytokines were measured in T cells purified from spleens or lymphoma tumors, stained with APC-conjugated mAbs against Perforin (eBiOMAK-D), TNFα (MP6-XT22), and IFNγ (XMG1.2) (eBioscience, San Diego, Calif.). Four-color flow cytometric analysis of $10^6$ cells was performed using the FACSCanto II (BD Biosciences, San Jose, Calif.).

T cell isolation. Spleens were harvested from euthanized animals and single cell suspensions were obtained by gently dissociating the splenic capsule over a 40 μm filter. Red cells were depleted by incubating with ACK Lysing Buffer (Lonza, Allendale, N.J.) and T cells isolated by negative selection on a LS⁺ column using the Pan T cell isolation kit on a MiniMACS Separator (Miltenyi Biotec, San Diego Calif.) as per manufacturer's instructions. T cell purity was assessed by flow cytometry and was always greater than 80%.

Vaccination and Tumor Challenge. C3d-positive and C3d-negative lymphoma cells (18-81 pre-B cell line were thawed and grown in vitro in selection medium (RPMI 1640 with 10% FCS; 2β-mercaptoethanol, 55 mM; Penicillin, 100U/ml and streptomycin, 100 μg/ml; L glutamine, 2 mM, Hygromycin, 1 mg/ml) for 6 days, before use. C3d-positive or C3d-negative B16-F0 cells were grown in RPMI1640 supplemented as detailed above with 5 μg/ml of puromycin instead of hygromycin. On the day of vaccination, cells were washed, suspended in fresh medium and viable cells were counted using Trypan Blue cell exclusion. Afterwards, tumor cells were irradiated with 10 Gy (IC-320 Irradiator, BSRB, University of Michigan) and then washed twice with PBS immediately before inoculation. Vaccine inoculations were, by i.p. injection of $5 \times 10^6$ lymphoma cells (twice, a week apart) into mice in the BALB/c genetic background, or by a single sub-cutaneous injection of $1 \times 10^7$ B16 melanoma cells into C57BL/6 mice. Lymphoma vaccinated mice were challenged with i.p. injection of $5 \times 10^3$ live tumor cells. Mice vaccinated with melanoma cells and their controls were challenged with s.c. injection of $2 \times 10^5$ live tumor cells, 35 days after the last vaccination with $10^7$ cells. Non vaccinated melanoma mice were challenged with s.c. injection of $4 \times 10^4$ live tumor cells. Mice were monitored daily.

Cellular Apoptosis assay. Cellular apoptosis was measured using a FAM-FLICA assay purchased from Immuno-Chemistry technologies, L.L.C., Bloomington, Minn., according to the manufacturer's instructions.

qPCR. RNA was obtained from regulatory T cells isolated from recipient mice 10 days or 18-20 days following tumor transfer, with a Midi MACS T cell isolation kit (Miltenyi Biotec, San Diego Calif.). Total RNA was prepared using PURELINK RNA Mini Kit (Ambion-ThermoFisher Scientific, Waltham, Mass.). cDNA was produced using the VILO kit (Invitrogen, ThermoFisher Scientific, Waltham, Mass.), according to the manufacturer's instructions. RT PCR was performed using TAQMAN primers (purchased from Life Technologies ThermoFisher Scientific, Waltham, Mass.) primer pairs. CR2-specific primers, Mm00801681_m1; CR1 specific primers; HPRT specific primers, Mm01545399_m1; PD-1 specific primers, Mm01285676_m1; Foxp3-specific primers, Mm00475162_m1. The PCR conditions were the recommended by the manufacturer, 50° C., 2', 95° C. for 10' followed by forty cycles of 95° C. for 15" and 60° C. for 1'.

T cell proliferation assays. T cells isolated from spleens of naïve BALB/c mice were stained with Vibrant CFDA SE (Invitrogen, Carlsbad, Calif.) prior to culture. CFDA SE was reconstituted with dimethyl sulfoxide (DMSO) to a final concentration of 5 mM. Cells were re-suspended in phosphate-buffered saline (PBS)+5% FCS (Gibco, Gaithersburg, Md.) at $5 \times 10^6$/mL and were incubated with CFDA SE for 5 minutes at room temperature. Incubation was stopped by placing cells on ice for 5 minutes, and cells were washed twice in ice-cold 5% FCS-RPMI and re-suspended in medium with final concentration $2 \times 10^6$ cells/mL prior to distribution into wells ($10^5$ in 100 μl/well) coated with 10 μg/ml anti-mouse CD3e, clone 145-2C11 (BD biosciences, San Jose, Calif.). Cells were stimulated with 1 μg/ml anti-mouse CD28, clone 37.51 (BD biosciences, San Jose, Calif.), IL2 (100 ng/ml) with or without 1:10 dilution of supernatant from C3d-positive or C3d-negative tumor cell cultures, with or without 10 μg/ml anti-mouse CR1/CR2 (7G6) mab or 10 μg/ml isotype control.

Tumor-Specific Killing by Cytotoxic T cells. Lymphocytes from the spleens and lymphoma were harvested from vaccinated mice 78 days after vaccination and 10 days after injection of lymphoma, as described above. Isolated T cells were cultured with tumor cells (irradiated with 10Gy) derived from the same clone that originated the lymphoma, in the presence of IL-2 for 6 days. Cytotoxicity was be measured against C3d-positive or C3d-negative targets at various E:T ratios by a standard LDH cytotoxicity assay (PIERCE, ThermoFisher Scientific, Waltham, Mass.), according to the manufacturer's instructions.

Statistical Considerations. All comparisons were done with Prism-Graphpad software (v6), Irvine, Calif. Comparison of survival curves was by the log rank Mantel Cox test. Averages were either compared by unpaired students T test (2 tailed) or by non-parametric Mann Whitney test, and when appropriate, with correction for multiple comparisons by Dunn's test. Contingency analysis was performed using linear or non-linear regression analysis with tools available in the Prism-Graphpad software. A P value less than 0.05 was considered significant.

Study Approval.

Animals were maintained in accordance with regulations of the University of Michigan Committee on the Use and Care of Animals under specific pathogen free condition.

Example 2

Figure 1A:
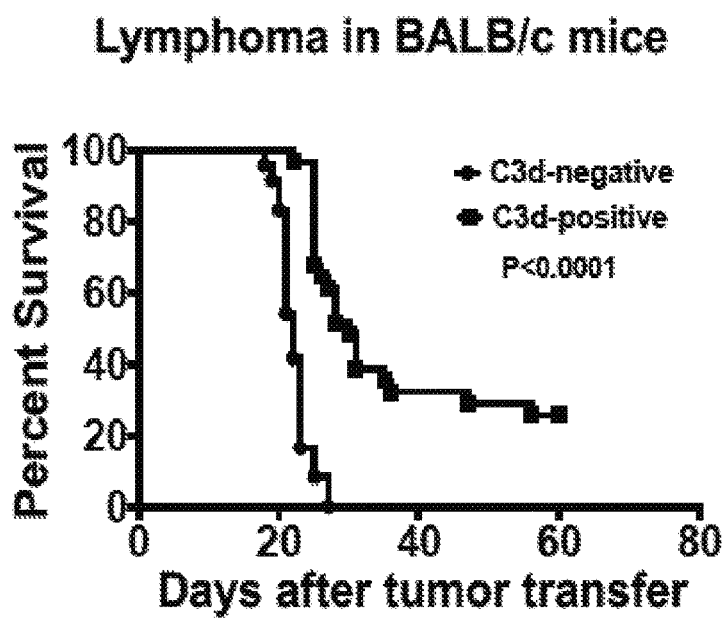
FIG. 1 shows that free C3d in tumor cells enhances resistance of mice to tumors by promoting adaptive immunity. (A) Survival of BALB/c mice challenged with $5 \times 10^3$ isogenic lymphoma cells expressing (N=31) or not expressing (N=24) free murine C3d. (B) Lymphoma tumor volumes 10 days after injection of $10^7$ C3d+ or C3d− cells. On average, C3d+ tumors were 176 mm$^3$ and C3d− tumors 523 mm$^3$. Data represent mean±SEM analyzed by Mann Whitney 2 tailed test. (C) H&E (upper panels) and immunofluorescence staining (lower panels) of lymphoma tissue. C3d+ and C3d− tumors have similar morphology (above) and both are recognized by antibodies against B220 (below, left and right sections) but only the transgenic C3d+ lymphoma stains with antibodies against an ENV fusion construct used to detect expression of C3d (below, right section). (D) Melanoma tumor volumes at various times after s.c. injection of $4 \times 10^4$ C3d+B16 (N=10), or $4 \times 10^4$ C3d− (N=9) melanoma cells in syngeneic mice. (E) Survival of recombinase activating gene 2 (RAG-2) deficient mice injected with $5 \times 10^3$ isogenic C3d+(N=15) or C3d− (N=15) lymphoma cells. (F) Survival of mice injected with $5 \times 10^3$ lymphoma cells of which 1-50% were C3d+. (G) Survival of B cell-deficient (JH−/−, κ−/−) mice challenged with $5 \times 10^3$ C3d−(N=8) or C3d+(N=9) tumor cells. (H) Schematic of the C3d expression vector (for B cell lymphoma). C3d expression was driven by the immunoglobulin lambda 1 light chain promoter and by the immunoglobulin heavy chain major intronic enhancer, as shown. (I) Lymphoid cells stably transfected with this vector expressed the C3d protein. Shown is a Western Blot analysis of lysate obtained from 40-60×10$^6$ cells. Lysates were run on 7.5% SDS PAGE gel and C3d expression detected by rabbit anti-mouse C3d (1:1000). Three C3d copies had an apparent molecular mass of 100 KD. (J) Quantification of C3d mRNA measured by qPCR in cultured tumor cells or explanted tumors. (K) Survival curves of mice injected with C3d+ or C3d− $5 \times 10^3$ tumor cells and either anti-CD4 and anti-CD8 monoclonal antibodies or with the respective isotype controls. (L) Figure shows that depletion of CD4 and CD8 T cells accelerates tumor growth and decreases survival of mice injected with C3d+ tumor cells. Immunofluorescence analysis of frozen sections of C3d+ or C3d− lymphoid tumors stained with anti-CD8 antibodies (right section). CD8+ T cells were enumerated by flow cytometry and results are shown in FIG. 3H. All survival curves are Kaplan-Meier plots and differences between curves were analyzed by the Logrank Mantel-Cox test.
Figure 1B:
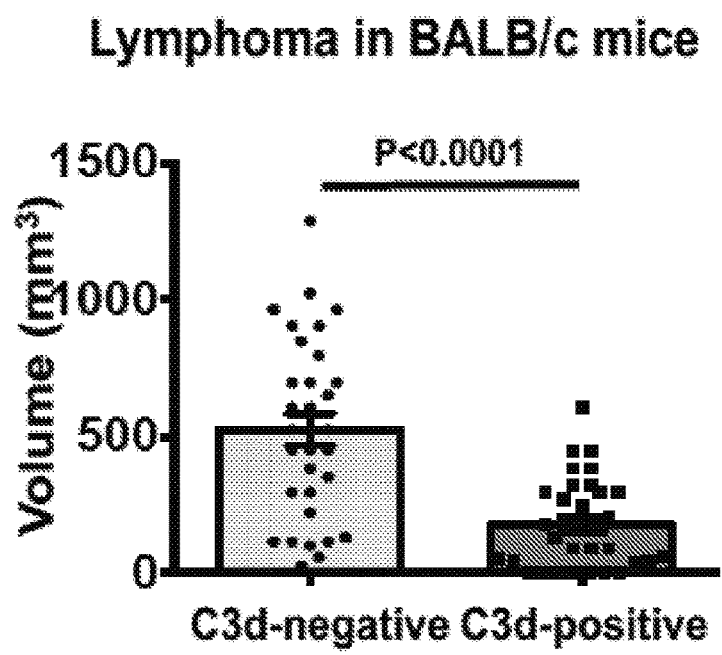
Figure 1C:
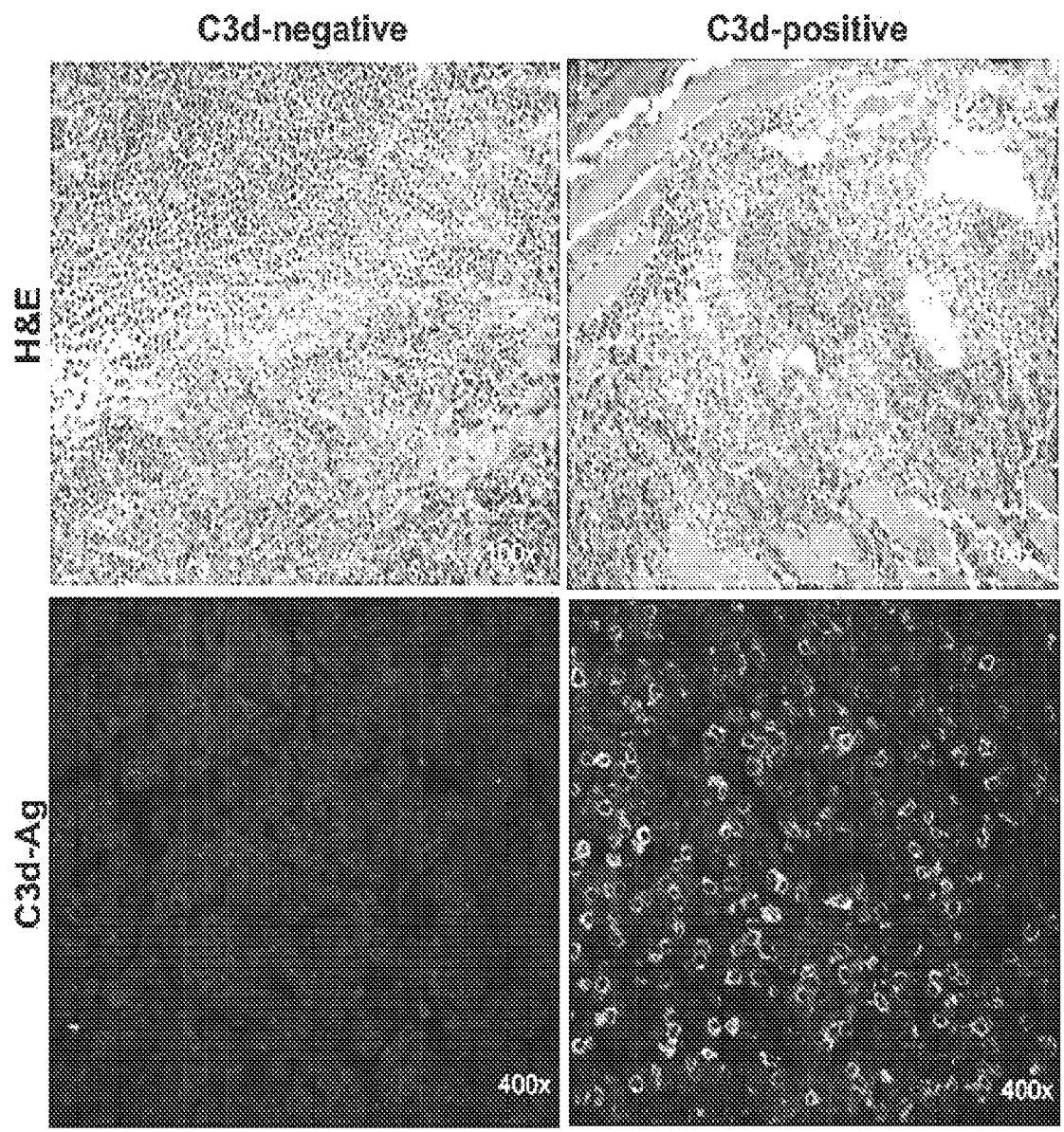
Figure 1D:
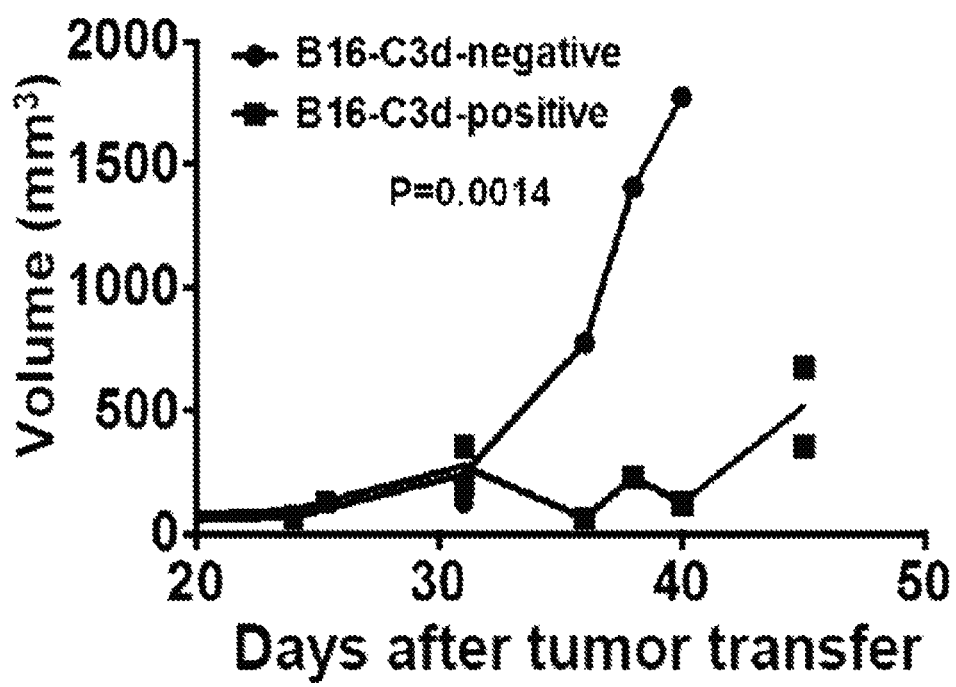
Figure 1E:
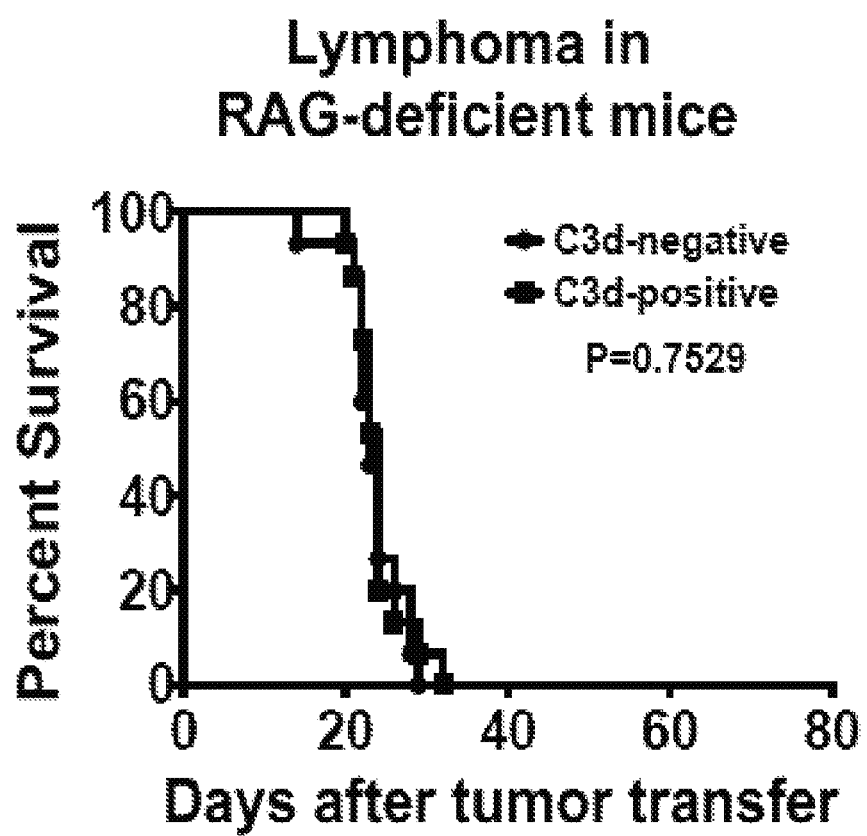
Figure 1F:
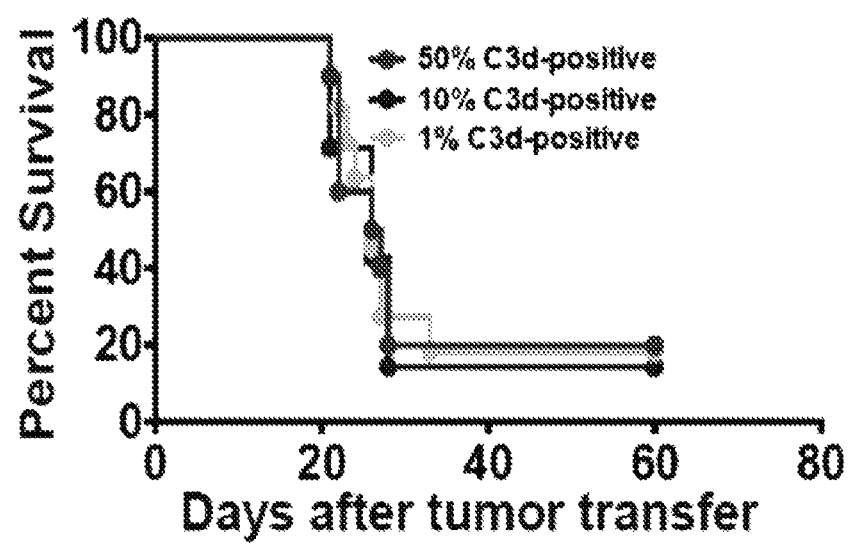
Figure 1G:
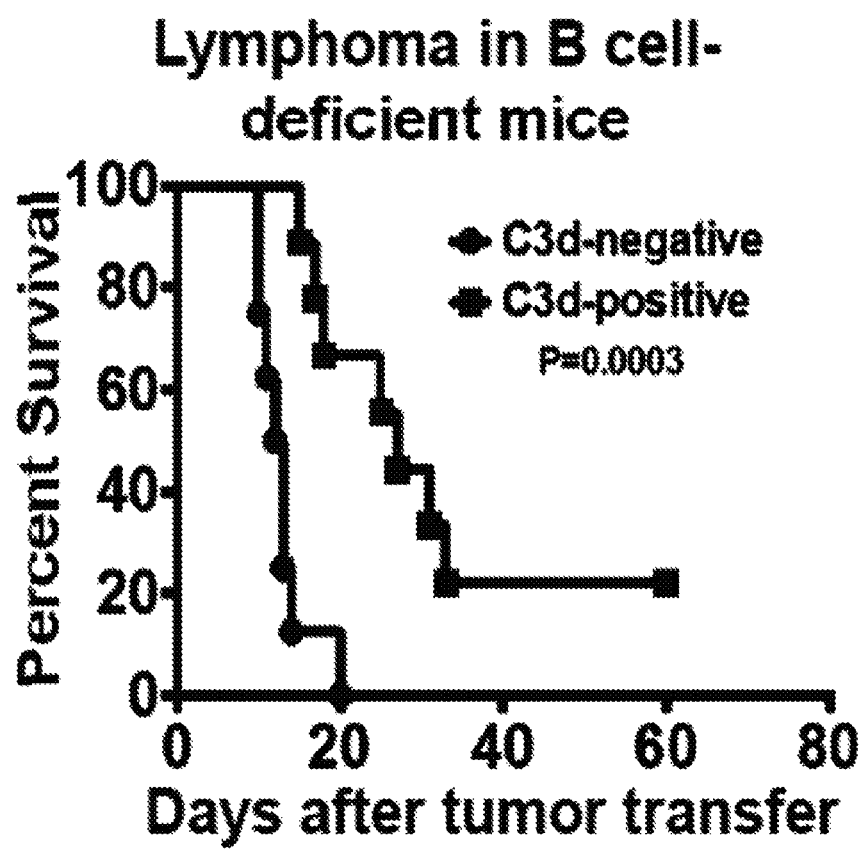
Figure 1H:
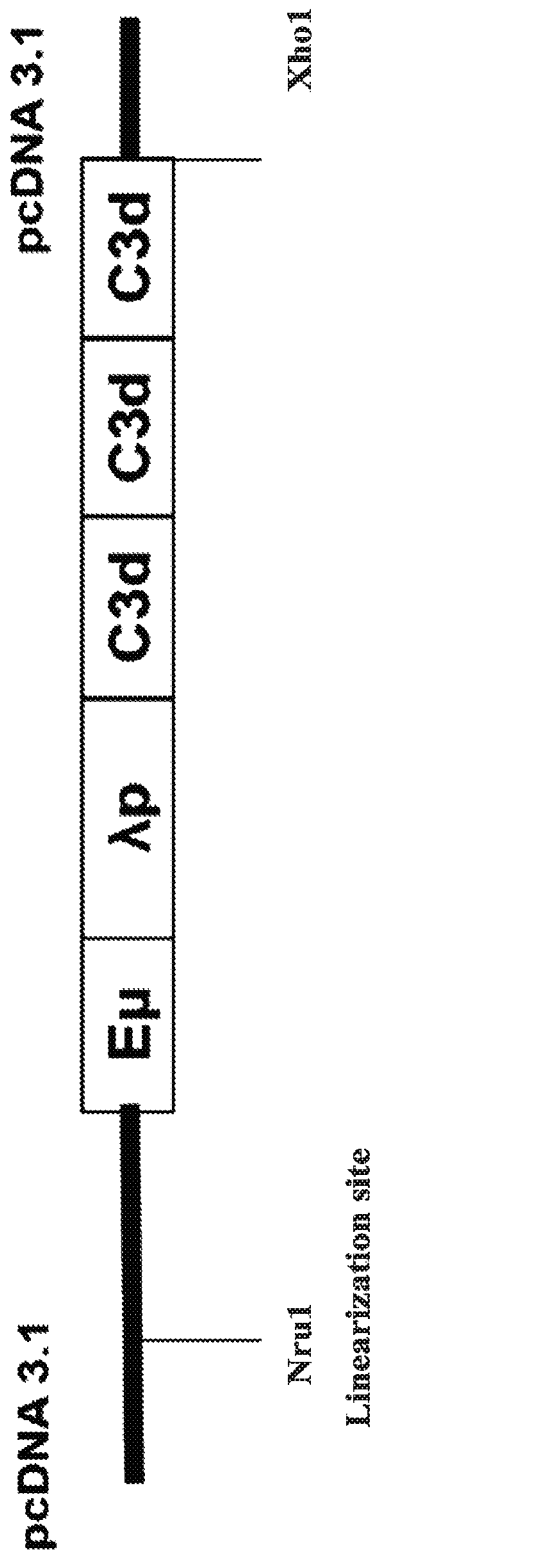
Figure 1I:
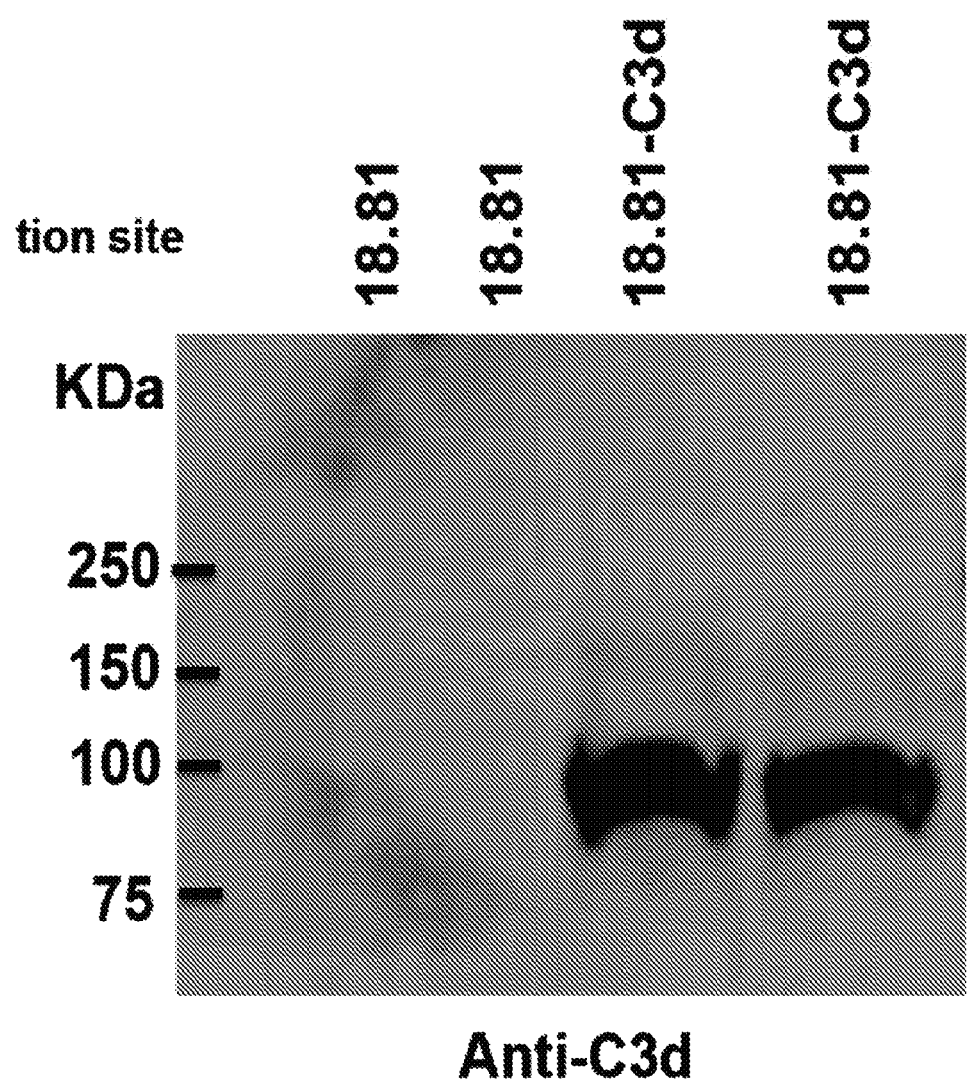
Figure 1J:
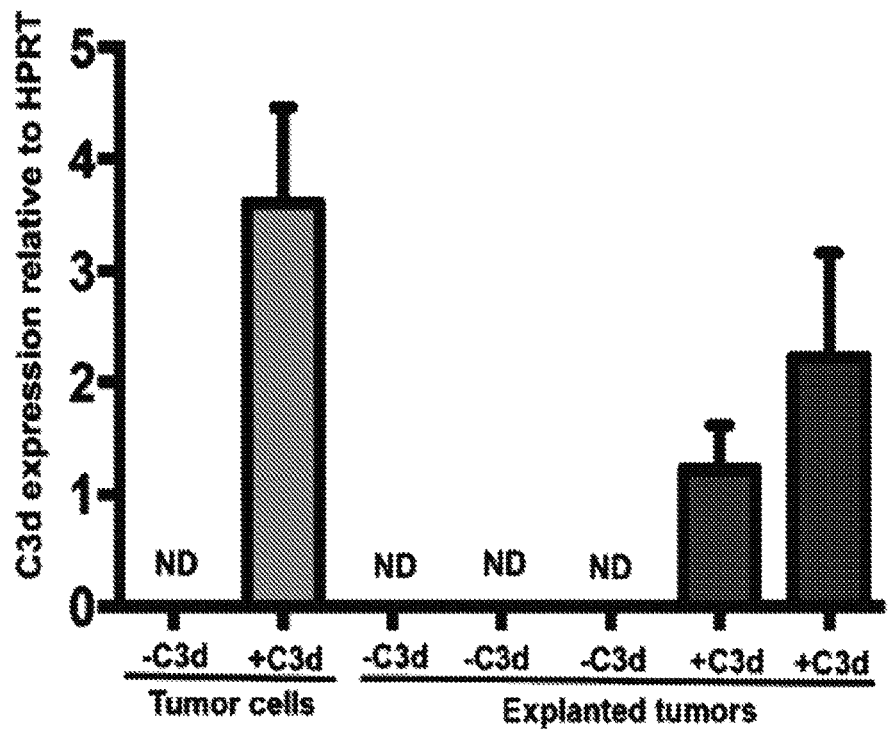
Figure 1K:
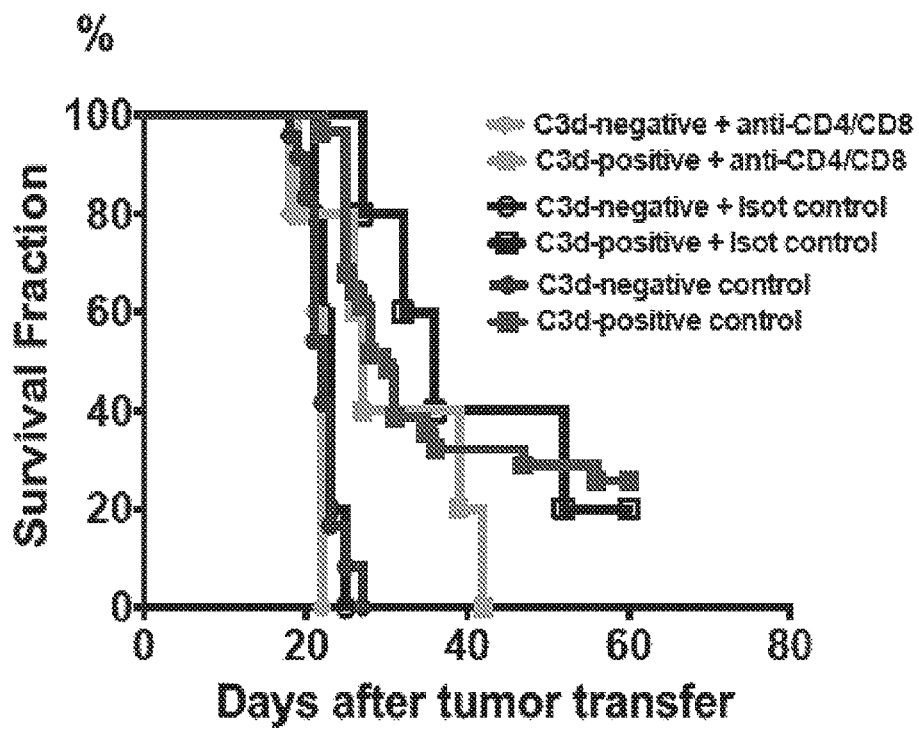
Figure 1L:
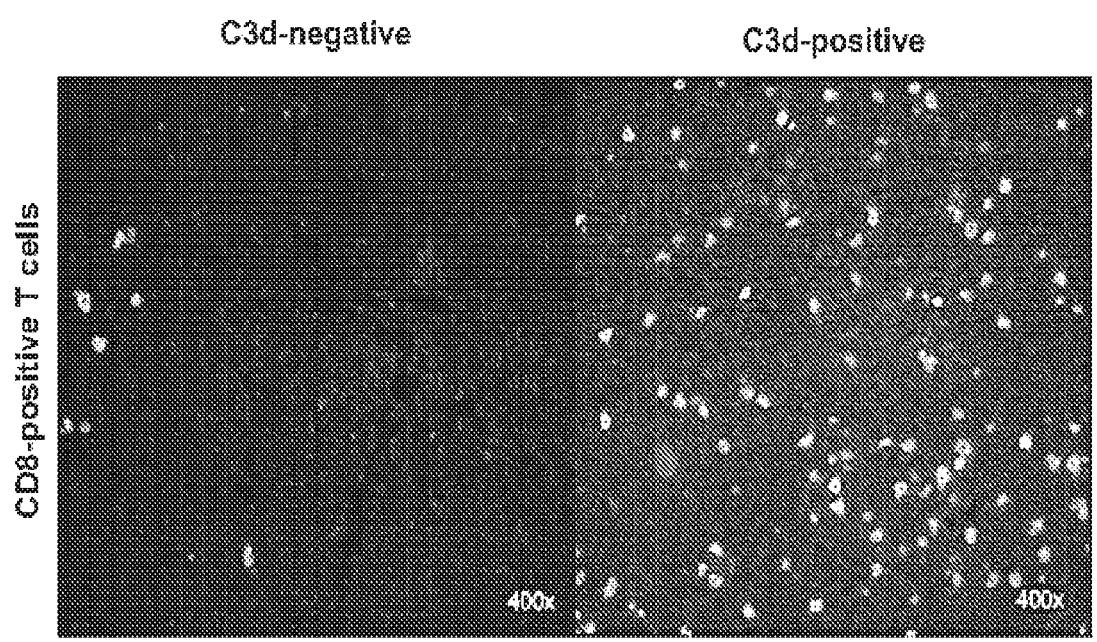
Figure 2A:
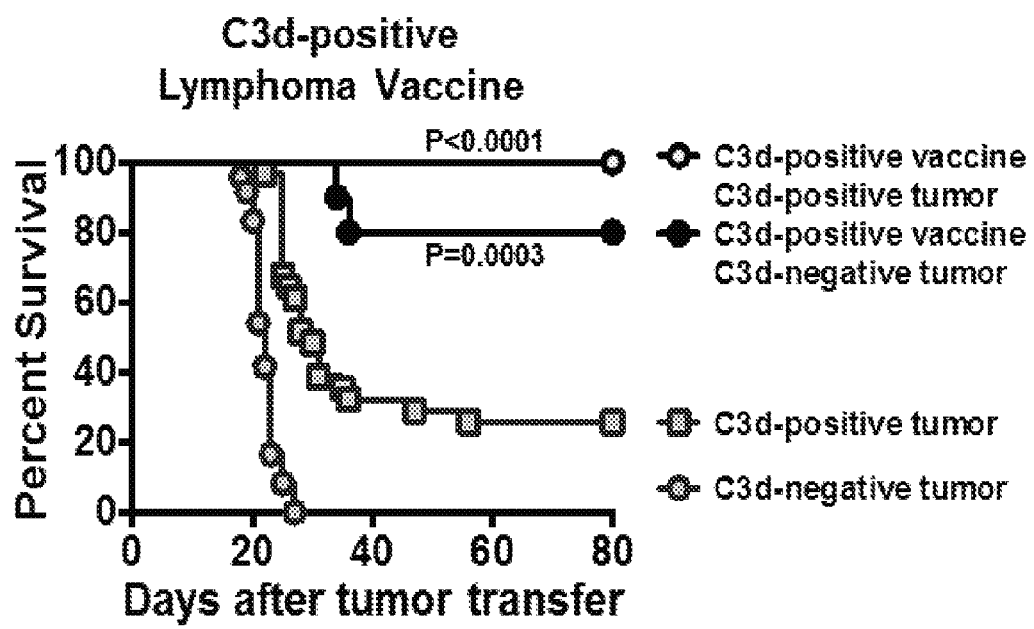
FIG. 2 shows that adaptive immunity evoked by vaccination with killed C3d+ tumor cells protects against lymphoma and melanoma. Mice were vaccinated with $10^7$ C3d+ or C3d-killed lymphoma followed by administration of living $5 \times 10^3$ C3d+ or C3d− lymphoma cells 35 days later (A-B), or with $10^7$ C3d+ or C3d− killed melanoma cells followed by transfer of $2 \times 10^5$ live melanoma cells 35 days later (C-F). (A) Survival of mice vaccinated with killed C3d+ lymphoma cells. (B) Survival of mice vaccinated with killed C3d− lymphoma cells. (C) Impact of C3d+ or C3d− vaccine on growth of C3d− melanoma. Data represent mean±SEM. Analysis was by Mann Whitney 2 tailed test. (D) Prevention of C3d− melanoma by vaccination with killed C3d+ or C3d− melanoma cells. Shown are Kaplan-Meier plots and differences between curves were analyzed by the Logrank Mantel-Cox test. (E) Impact of vaccination on growth of C3d− melanoma estimated by tumor size at death (sacrifice) or at 21 days, in mice that were alive at 21 days. All non-vaccinated mice and 8 of 10 mice vaccinated with C3d− melanoma died or were sacrificed at 18 or 19 days for humane reasons. 4/10 of C3+-vaccinated mice either had no apparent tumors or smaller tumors at sacrifice (21 days). (F) Photographs of C3d− melanoma tumors excised at indicated days after tumor inoculation in mice vaccinated with C3d+ or C3d− irradiated melanoma cells. (G) Shown is a photograph of an incipient tumor growing subcutaneously (inset) in mice vaccinated with C3d+ melanoma cells, 21 days after tumor inoculation. Data represent mean±SEM. Analysis was by Mann Whitney 2 tailed test.
Figure 2B:
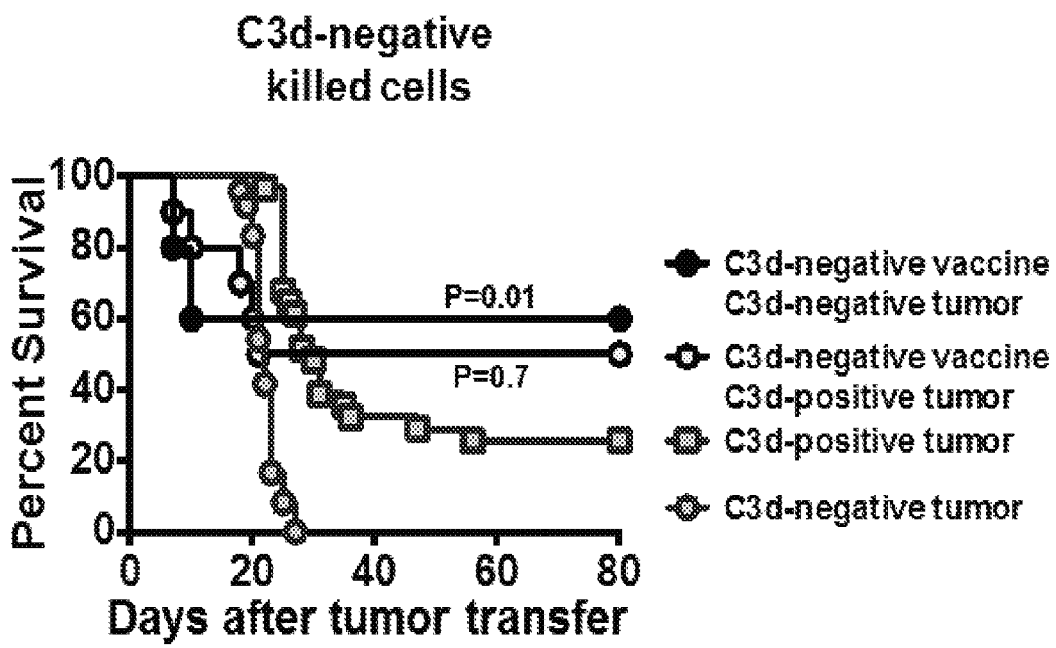
Figure 2C:
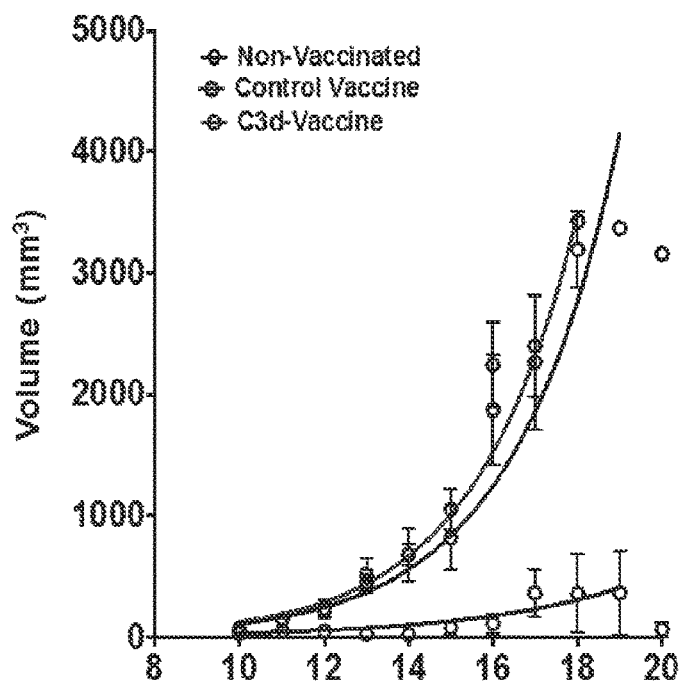
Figure 2D:
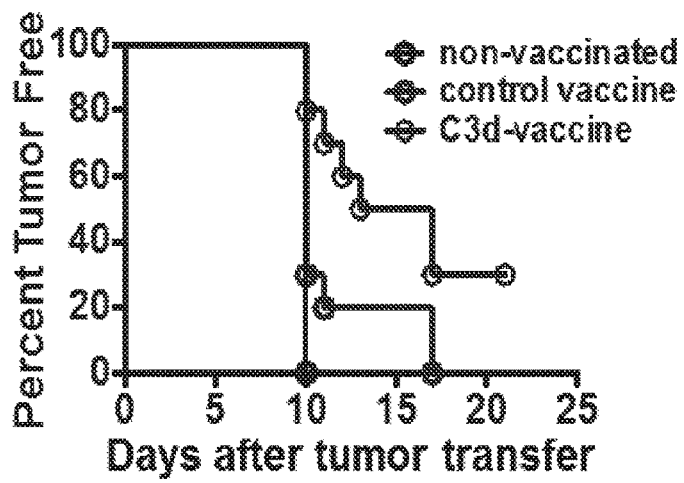
Figure 2E:
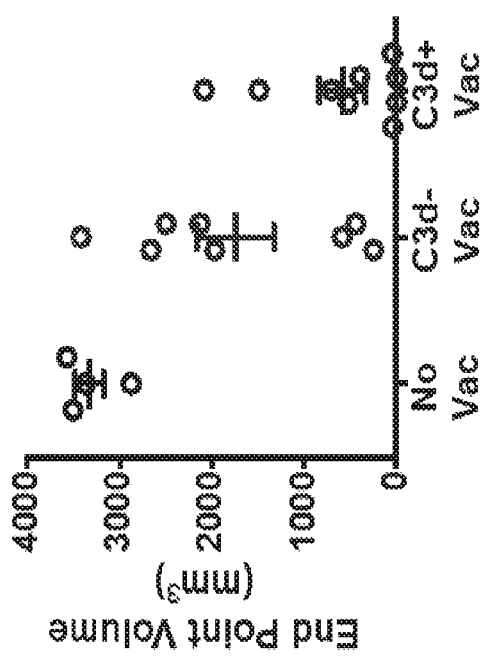
Figure 2F:
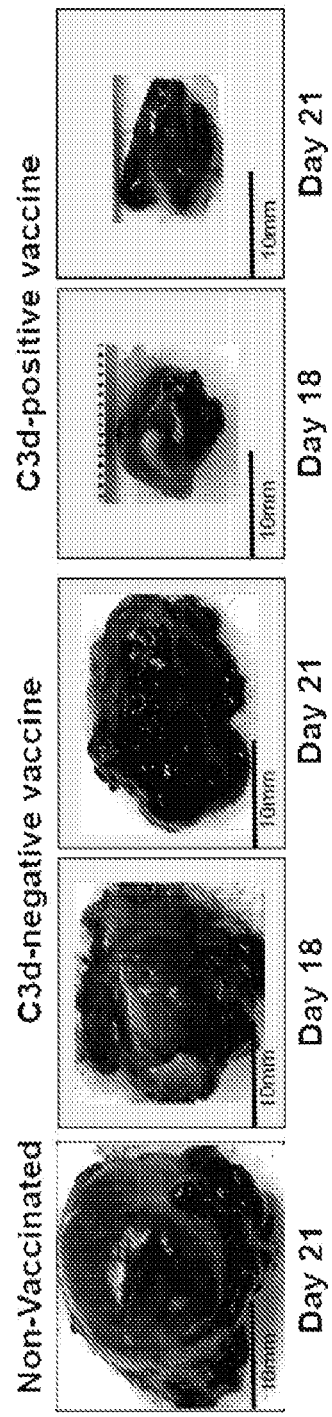
Figure 2G:
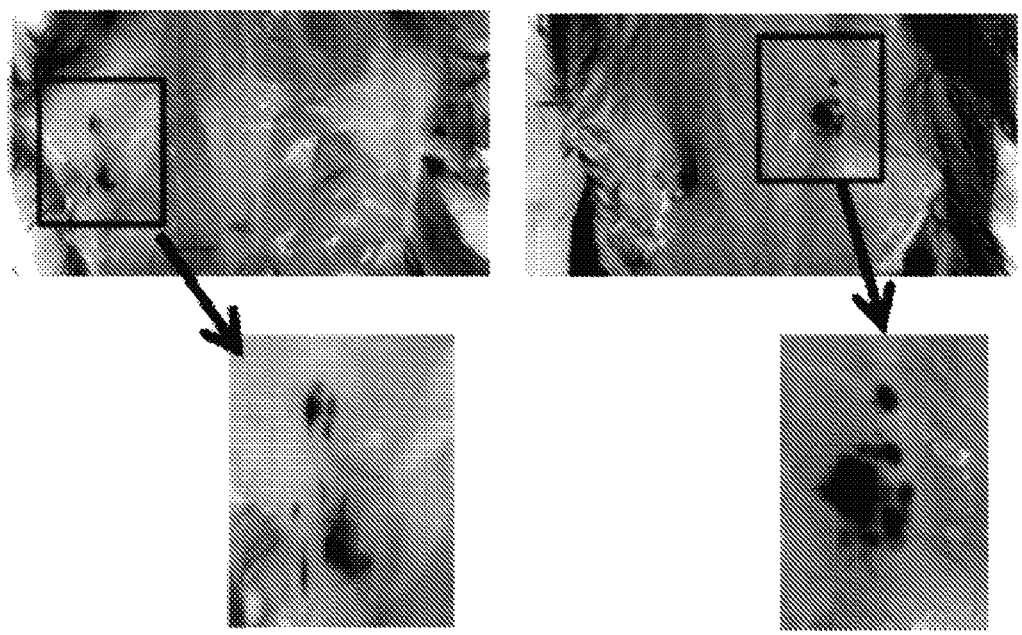

C3d-Expression in Tumor Cells Evokes Tumor-Specific Immune Responses that Alter Tumor Growth and Development While studying immunity to C3d-linked viral antigens expressed in murine lymphoma cells in mice, it was observed that expression of C3d alone slowed growth of lymphomas and enhanced survival of tumor-bearing mice (See FIGS. 1A-1C). C3d-negative lymphomas injected into the peritoneum of isogeneic mice rapidly generated abdominal masses that invaded spleen and muscle and caused death 18 to 27 days later. However, when lymphoma cells expressing C3d were administered, survival was prolonged (P<0.0001) and in ¬25% of mice the lymphomas resolved spontaneously. C3d-expression on tumor cells was tested by Western blot (See FIGS. 1H and 1I) and by qPCR (See FIG. 1J). Expression of C3d in B16 melanoma cells also slowed tumor growth and prolonged survival of mice in which the cells were introduced (See FIG. 1D). However, the presence of C3d in tumor cells and its manner of expression had no direct impact on tumor growth or intrinsic cellular resistance as C3d-positive and C3d-negative lymphomas progressed and death ensued at the same rate after tumor cells were introduced into RAG-deficient mice (See FIG. 1E), and because the presence of C3d even in a small fraction of tumor cells slowed and in some cases prevented the lethality of lymphomas consisting predominantly of C3d negative cells (See FIG. 1F).

The benefit conferred by C3d depended on that protein because it was vitiated by administration of CR2-Ig, which binds to and blocks C3d interactions with CR2, its cognate receptor (See Table 1).

TABLE 1

Percent survival of mice dependent upon interaction between C3d and CR2.

|  | C3d-positive | C3d-positive + CR2-Ig | C3d-negative | C3d-negative + CR2-Ig |
|---|---|---|---|---|
| % survival after 15 days | 60% (N = 5) | 0% (N = 5) | 0% (N = 5) | 0% (N = 5) |
| P value Log-rank (Mantel Cox) test |  | P = 0.001 |  | P = 0.119 |

The absence of any benefit of C3d expression in lymphomas in immunodeficient mice (See FIG. 1E) also indicated that C3d might, in some way, facilitate immune surveillance. Protection invoked by C3d however did not depend on B cells or follicular dendritic cells because it was undiminished when C3d-positive tumor cells were introduced into B cell and Ig-deficient JH−/−, κ−/− mice (See FIG. 1G) but did depend on T cells, since a single infusion of monoclonal anti-CD4 and anti-CD8 suppressed protection, at least in part (See FIG. 1K), and C3d-positive lymphomas were infiltrated with CD8+ T cells while those cells were very rare in C3d-negative lymphomas (See FIG. 1L).

In order to confirm that C3d-mediated protection reflected an adaptive immune response, it was determined whether prior exposure to killed tumor cells expressing C3d generated more effective immunity. Vaccination with killed C3d-positive tumor cells prevented development of lymphoma in all mice given living C3d-positive tumor cells (P<0.0001) and in 80% of the mice given C3d-negative living tumor cells (P=0.0003), 35 days later (See FIGS. 2A and 2B). In contrast, vaccination with killed C3d-negative tumor cells did not protect mice given living C3d-positive tumor cells (P=0.7) and failed to protect 40% of the mice given C3d-negative living tumor cells (P=0.01) (See FIGS. 2A and 2B). Protective anti-tumor immunity was not directed at C3d since mice vaccinated with killed C3d-positive cells resisted C3d-negative lymphomas to nearly the same extent as C3d-positive lymphomas. Vaccination with killed C3d-expressing melanoma cells delayed the growth of C3d-negative tumors (See FIG. 2C) and prevented the development of melanomas in 30% of mice (See FIG. 2D). Mice were sacrificed 21 days after tumor injection or when tumor size exceeded 10 mm in diameter, or ulcerated. At the time of sacrifice, mice vaccinated with killed melanoma cells expressing C3d had, on average, 5.7 fold smaller lymphomas than non-vaccinated mice and 3 fold smaller lymphoma than mice vaccinated with C3d-negative melanoma cells (See FIGS. 2E-2G). Thus, in some embodiments, the invention provides that C3d vaccination (e.g., vaccination with C3d-expressing tumor cells) evokes a long-lasting immune response that protects against tumor growth, often preventing it.

If C3d enhances protective cellular immunity, it was postulated that it does so by interaction with CR2, a specific receptor for that protein. Human and murine T cells can express CR2; but, which T cells express CR2 and how CR2 influence T cell responses has been unclear with speculation touching on T cell development, activation, regulation and viral infection. At baseline, <2% of T cells from the spleen of BALB/c mice expressed CR2 based on binding of 7G6 antibodies specific for CD21. Although 7G6 binds both to CR2 and CR1, qPCR was used to confirm that only CR2 is produced by T cells. Thus, it was tested which T cells express CR2, and whether expression changes after introduction of C3d-positive lymphomas. As FIG. 3A shows, CR2 expression was notably increased, albeit transiently, in regulatory (CD4+, Foxp3+) T cells after introduction of C3d-positive tumor cells, but not after introduction of C3d-negative lymphoma cells (P=0.01) relative to expression by naive regulatory T cells. FIGS. 3B and 3F show that C3d-positive lymphomas have fewer CD21+(CR2+) Treg than C3d-negative lymphomas, 10 days after tumor inoculation. FIGS. 3C and 3G shows that CD21+ (CR2+) Treg in C3d-positive lymphomas are more frequently apoptotic than those in C3d-negative lymphomas (P=0.0003) indicating that exposure to C3d associated with lymphoma cells induces the apoptosis of CD21+ (CR2+) expressing Treg and in this way, reduce their impact in the suppression of anti-tumor immunity. Consistent with the possibility that C3d clears Treg, C3d-positive lymphomas contained fewer Treg than C3d-negative lymphomas at 18 days (see FIGS. 3D and 3E) (P<0.0001). Although CD8+ T cells did not express CR2, CD8+ T cells were more frequent in C3d-positive lymphomas and rare on C3d-negative lymphomas (FIG. 1H) and more frequently apoptotic in C3d-negative lymphomas (FIG. 3I), indicating that C3d expressed by lymphomas prevent apoptosis of CD8+ intra-tumor lymphocytes.

Figure 4A:
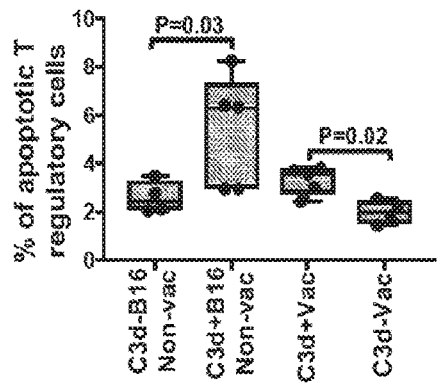
FIG. 4 shows the impact of C3d on CD21 expression by regulatory T cells (Treg), on apoptosis of T reg and on Treg frequencies following vaccination against melanoma. Graphs reflect analysis of lymphocytes obtained from tumor draining lymph nodes of mice 14 days after tumor transfer. Mice were vaccinated by injection of $10^7$ killed melanoma cells 35 days prior to transfer of $2 \times 10^5$ live tumor cells.
Figure 4B:
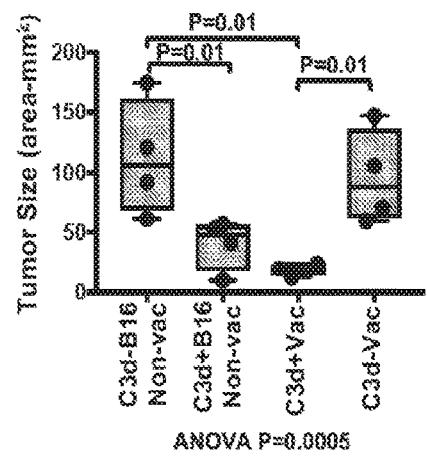

Next, it was determined whether vaccination with C3d-positive killed melanoma cells promoted apoptosis of Treg following tumor challenge. FIG. 4A shows that vaccination with C3d-positive killed melanoma cells promoted apoptosis of Treg in the draining lymph nodes, while vaccination with C3d-negative killed melanoma cells did not (p=0.02). As observed in the lymphoma model, C3d-positive melanomas had more frequent apoptotic Treg than C3d-negative melanomas (p=0.03) 14 days after tumor challenge (See FIG. 4A). Vaccination with C3d-positive killed melanoma cells reduced, by six fold, the size of C3d-negative melanomas 14 days after tumor challenge compared to melanomas grown in non-vaccinated hosts, and by five fold compared to vaccination with C3d-negative melanoma cells (See FIG. 4B). In contrast, C3d-negative melanoma vaccination did not reduce B16 tumor growth, as the average tumor size after vaccination was almost identical to the average tumor size in non-vaccinated mice (See FIG. 4B). FIGS. 4A and 4B also show that the frequency of apoptotic regulatory cells varies reciprocally with tumor size, the smaller the tumor, the more frequent apoptotic regulatory T cells are within each group. FIG. 5 shows that expression of C3d by melanoma cells yielded smaller lymphoma with larger necrotic areas, greater infiltration by CD4+ and CD8+ lymphocytes and fewer Foxp3+ cells (See FIGS. 5B, 5F, 5J and 5N) compared to C3d-negative melanomas (See FIGS. 5A, 5E, SI and 5M). FIG. 5 shows that vaccination with C3d-positive killed melanoma cells was more effective at causing involution of C3d-negative melanomas (generated by injection of tumor cells 35 days after vaccination), at promoting infiltration of CD4+ and CD8+ lymphocytes and decreasing Foxp3+ cells (See FIGS. 5D, 5H, 5L and 5P) than vaccination with C3d-negative killed melanoma cells (See FIGS. 5C, 5G, 5K and 5O).

Figure 4C:
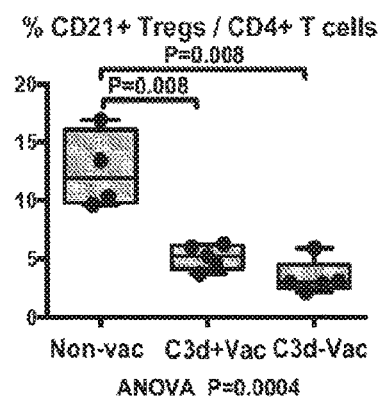
Figure 4D:
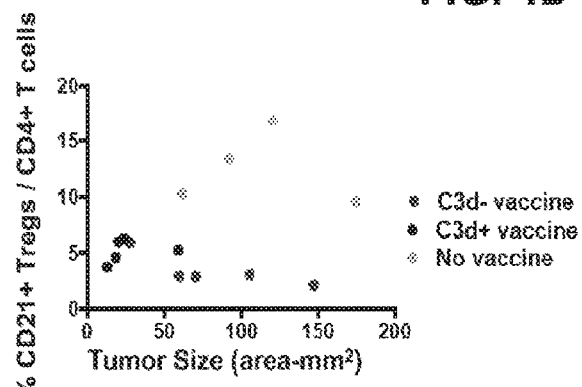
Figure 4E:
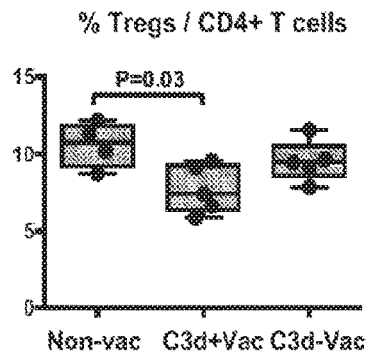
Figure 4F:
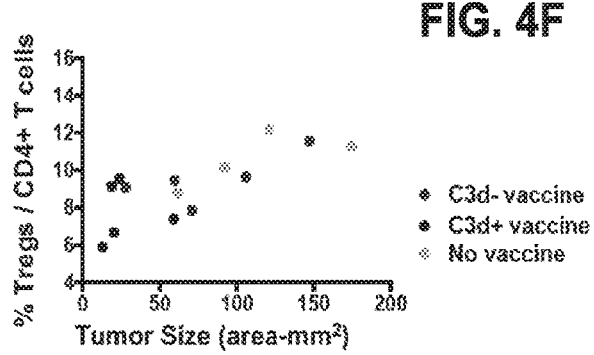

Both C3d-positive and C3d-negative vaccines decreased the frequency of CR2+ Treg in lymph nodes draining melanomas compared to the frequencies in non-vaccinated mice (See FIGS. 4C and 4D). Treg CR2 expression was independent of vaccination since unvaccinated mice expressed the highest frequency of CR2+ Treg, and Treg CR2 expression increased with the size of the tumor (See FIGS. 4C and 4D). In mice given C3d-negative melanoma vaccines the frequency of CR2+ Treg was independent of the size of the tumor (See FIG. 4D) while in mice given C3d-positive vaccines the frequency of CR2+ Treg and tumor size were decreased (See FIG. 4D). FIG. 4E shows that C3d-positive vaccines, but not C3d-negative vaccines, reduced the frequency of Treg in the tumor draining lymph nodes indicating C3d-positive vaccines selectively promote apoptosis of CR2+ Treg, in agreement with results described above. Consistent with this concept, tumor size increased in parallel with the frequency of Treg (See FIG. 4F).

Interaction of C3d with CR2 was identified to have another important function. Increased expression of CR2 correlated with dramatically decreased expression of PD-1 (See FIGS. 6A and 6B), which silences effector T cells by engaging PD ligand-1 (PD-L1). Consistent with an impact of C3d on this pathway, C3d-positive tumors had increased frequencies of infiltrating T cells producing perforin, TNF a and interferon γ (See FIGS. 6C and 6D) and T cells isolated from C3d-positive tumors exhibited increased cytotoxicity against C3d-negative tumor cells (See FIG. 6E).

Figure 7C:
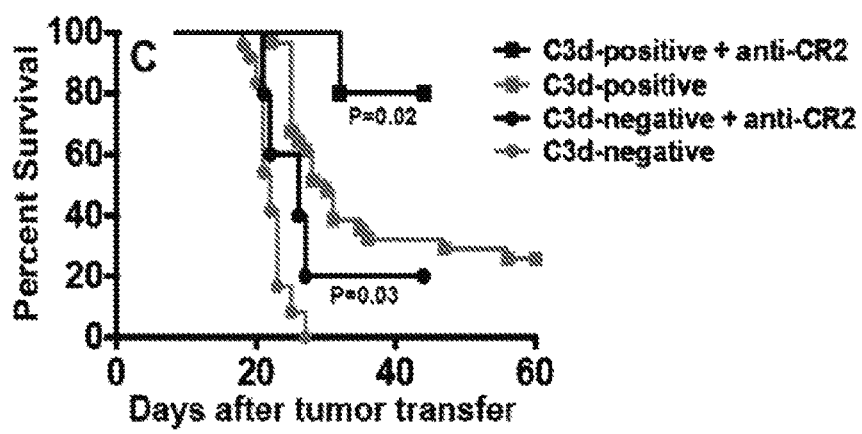

It was next determined if free C3d polypeptide exerts a discernable impact on responses of isolated T cells. Addition of C3d to naïve CD4+ T cells caused a modest increase in proliferation and this increase was greatly potentiated by anti-CR2 antibodies with agonist properties (See FIGS. 7A and 7B). C3d and anti-CR2 also inhibited Treg differentiation (See FIG. 7A). In support of the idea that engaging CR2 facilitates the generation of protective immunity, injection of anti-CR2 (7G6) antibodies, which deliver signals through CR2, improved survival of mice inoculated with C3d-negative (P=0.03) lymphoma or C3d-positive (P=0.02) lymphoma delivered at the same time (FIG. 7C).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in relevant fields are intended to be within the scope of the following claims.

What is claimed is:

1. A method of inducing an immune response to cancer in a subject comprising administering to the subject a therapeutically effective amount of a immunogenic composition comprising a population of cancer and/or tumor cells modified to express and/or harbor C3d, wherein said C3d is a C3d polypeptide, a C3d polypeptide oligomer or a C3d modified via conjugation of all or a portion of said C3d to a protein transduction domain (PTD) and/or cell penetrating peptide (CTP), and wherein said C3d is not part of a chimeric molecule encoding one or more specific antigens.

2. The method of claim 1, wherein the population of cells are genetically modified to express the coding sequence of C3d.

3. The method of claim 1, wherein the cancer and/or tumor cells are derived from the subject in which the composition for generating an immune response is administered.

4. The method of claim 1, wherein the immunogenic composition is co-administered with a cancer therapeutic agent.

5. The method of claim 2, wherein the population of cells genetically modified to express the coding sequence of C3d are lymphoma cells and/or melanoma cells.

6. A method of therapeutically treating cancer in a subject comprising administering to the subject a therapeutically effective amount of a pharmaceutical composition comprising: a) an immunogenic composition comprising a population of cancer and/or tumor cells modified to express and/or harbor C3d, wherein said C3d is a C3d polypeptide, a C3d polypeptide oligomer or a C3d modified via conjugation of all or a portion of said C3d to a protein transduction domain (PTD) and/or cell penetrating peptide (CTP), and wherein said C3d is not part of a chimeric molecule encoding one or more specific antigens; and b) a carrier and/or excipient; wherein administration of the pharmaceutical composition induces a cancer-specific immune response in the subject.

7. The method of claim 6, wherein administration of the pharmaceutical composition to the subject results in a detectable reduction in the number of tumor cells in the subject.

8. The method of claim 6, wherein the cancer-specific immune response comprises reduction in the number of T regulatory cells in the subject.

9. The method of claim 6, wherein the cancer-specific immune response comprises suppression of PD-1 and/or PDL-1 expression in the subject.

10. The method of claim 6, wherein the cancer-specific immune response comprises generation of tumor-specific, cytotoxic T cells.

11. The method of claim 6, wherein the cancer and/or tumor cells of the immunogenic composition are derived from a subject different from the subject in which the pharmaceutical composition is administered.

12. The method of claim 6, wherein the cancer and/or tumor cells of the immunogenic composition are a tumor cell line.

* * * * *